United States Patent [19]
Yerys

[11] Patent Number: 5,840,078
[45] Date of Patent: Nov. 24, 1998

[54] METHOD AND APPARATUS FOR MECHANICAL ATTACHMENT OF SOFT TISSUE TO BONE TISSUE

[76] Inventor: Paul Yerys, 30 Merrick Ave., East Meadow, N.Y. 11554

[21] Appl. No.: 396,570

[22] Filed: Mar. 1, 1995

[51] Int. Cl.⁶ .................................................. A61B 17/00
[52] U.S. Cl. .............................. 606/151; 606/65; 606/73; 411/60; 411/176; 411/184; 411/188; 24/453
[58] Field of Search ............................... 606/232, 72, 73, 606/75, 60, 53, 65, 66, 67, 68, 63, 151; 623/13, 11; 411/60, 166, 169, 176, 183, 184–188; 24/453

[56] References Cited

U.S. PATENT DOCUMENTS

| | | | |
|---|---|---|---|
| 769,184 | 9/1904 | Reeve | 411/184 |
| 4,350,465 | 9/1982 | Lovisek | 411/186 |
| 4,484,570 | 11/1984 | Sutter et al. | 606/60 |
| 5,141,520 | 8/1992 | Goble et al. | 606/60 |
| 5,370,662 | 12/1994 | Stone et al. | 606/232 |
| 5,403,333 | 4/1995 | Kaster et al. | 606/219 |

FOREIGN PATENT DOCUMENTS

| | | | |
|---|---|---|---|
| 42312 | 12/1923 | United Kingdom | 411/176 |

Primary Examiner—Jeffrey A. Schmidt

[57] ABSTRACT

Presented is a metallic cannulated rivet adapted for implantation in a bone mass through use of arthroscopic or open surgery for attachment of soft tissue thereto. The rivet in a first configuration is implanted, following which, a portion of the implanted rivet projecting from the bone site and penetrating the soft tissue is reformed in situ to clamp the soft tissue to the bone site. In a second aspect, the invention comprises the method and instrumentalities for effecting implantation of the rivet and reformation thereof in situ to mechanically clamp the soft tissue to the bone site. The method includes forming a small portal or incision to expose and prepare the bone site, torn or severed soft tissue is mobilized to intimately contact the bone site, the soft tissue is retained in proper position and a K-wire is advanced through the portal to penetrate the soft tissue and the bone mass to a predetermined depth and mark the point of implantation of the cannulated rivet. Thereafter, the rivet in its first configuration is advanced along the K-wire and inserted through the formed aperture in the soft tissue and anchored in the bone mass at the bone site with its proximate end projecting above the soft tissue. The head of the rivet is next reformed to clamp the soft tissue to the bone site, and the portal is closed.

23 Claims, 12 Drawing Sheets

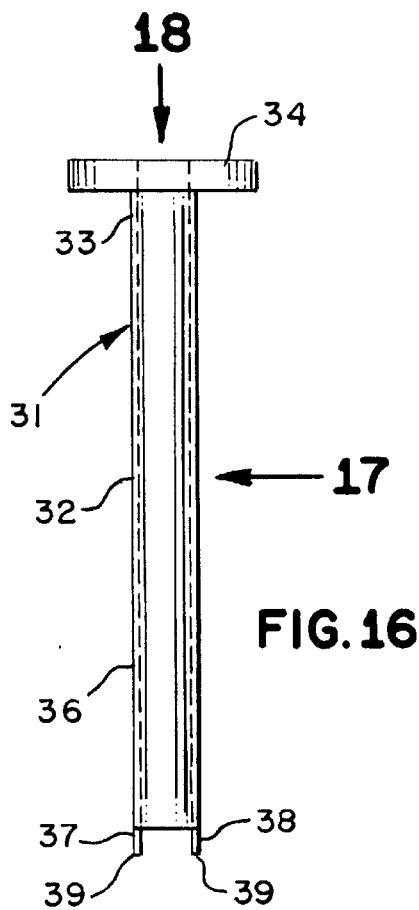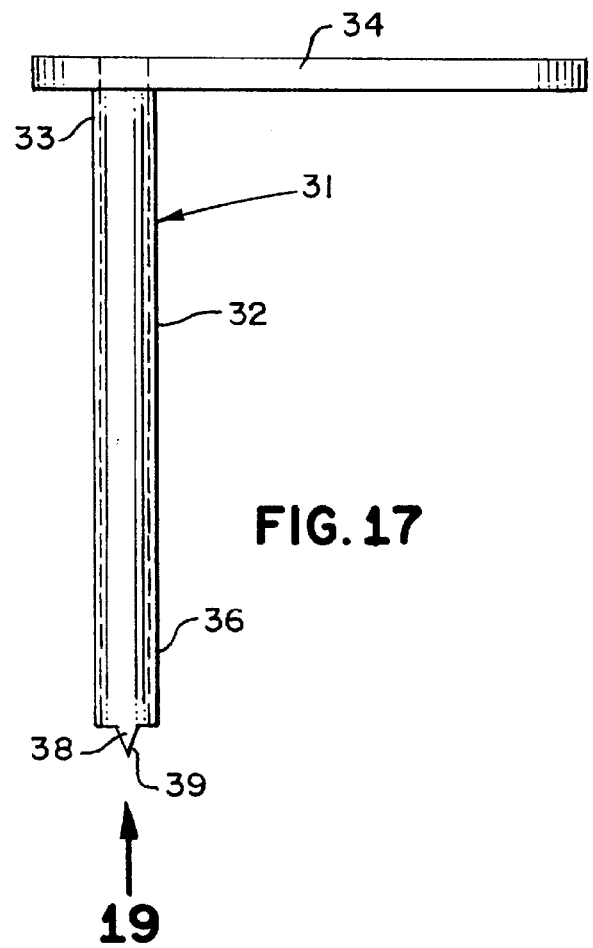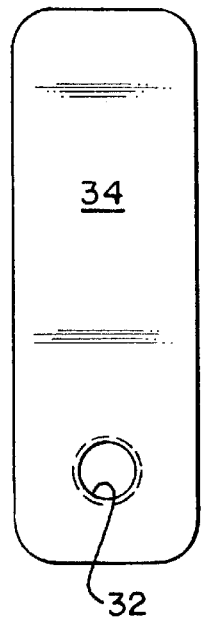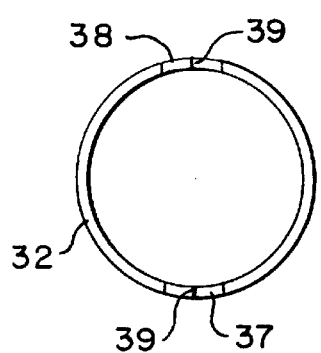
FIG. 16
FIG. 17
FIG. 18
FIG. 19

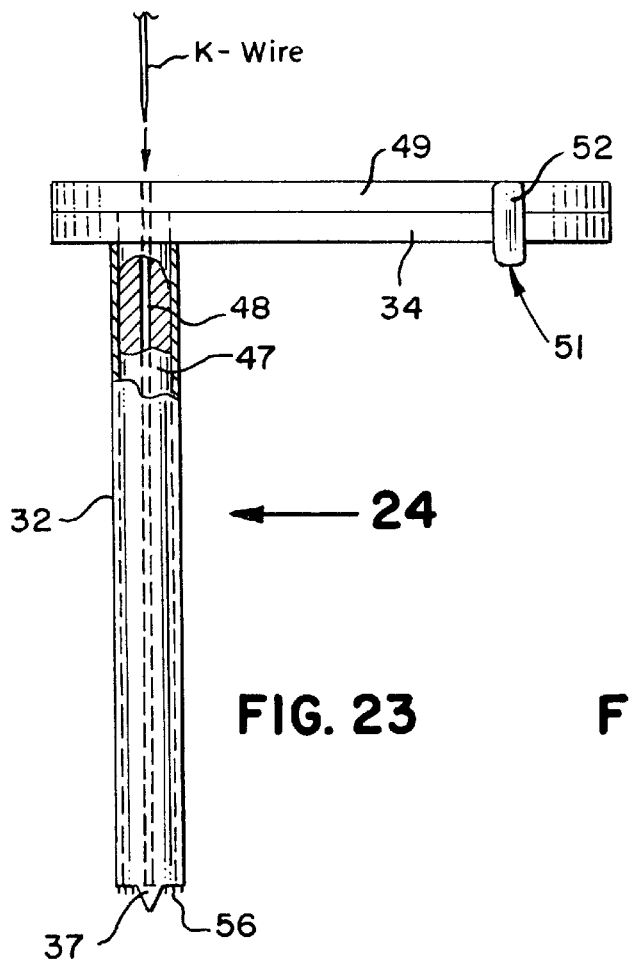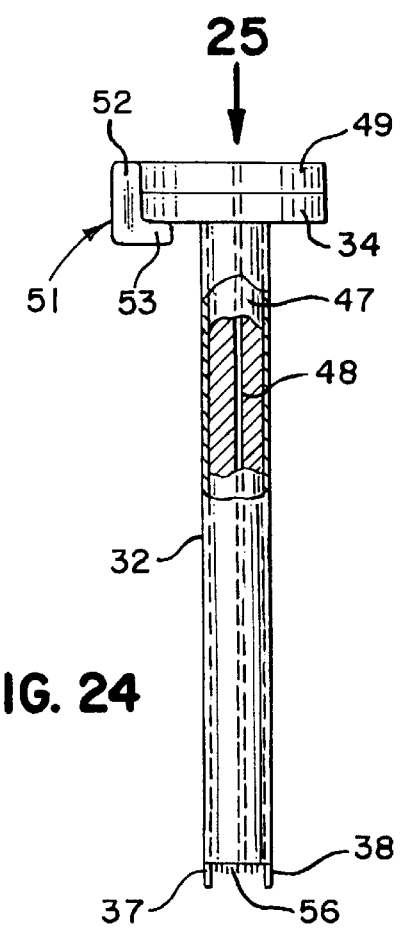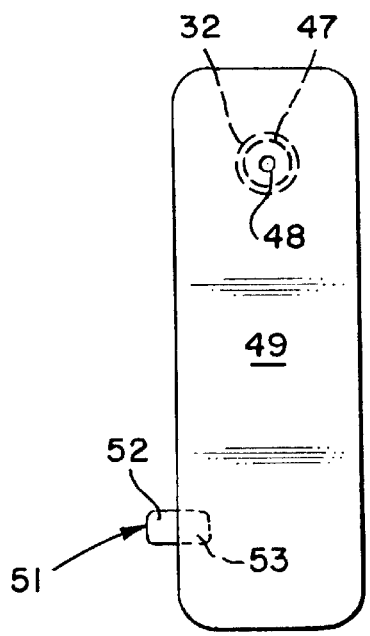

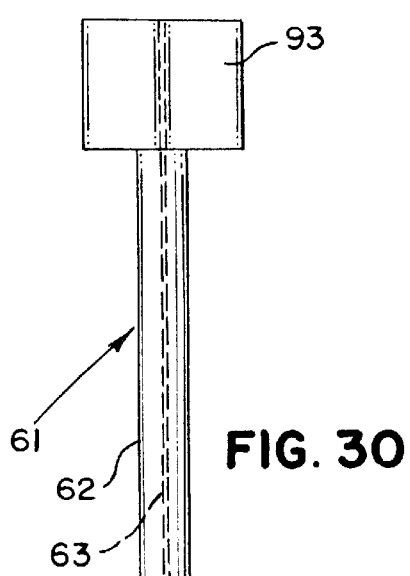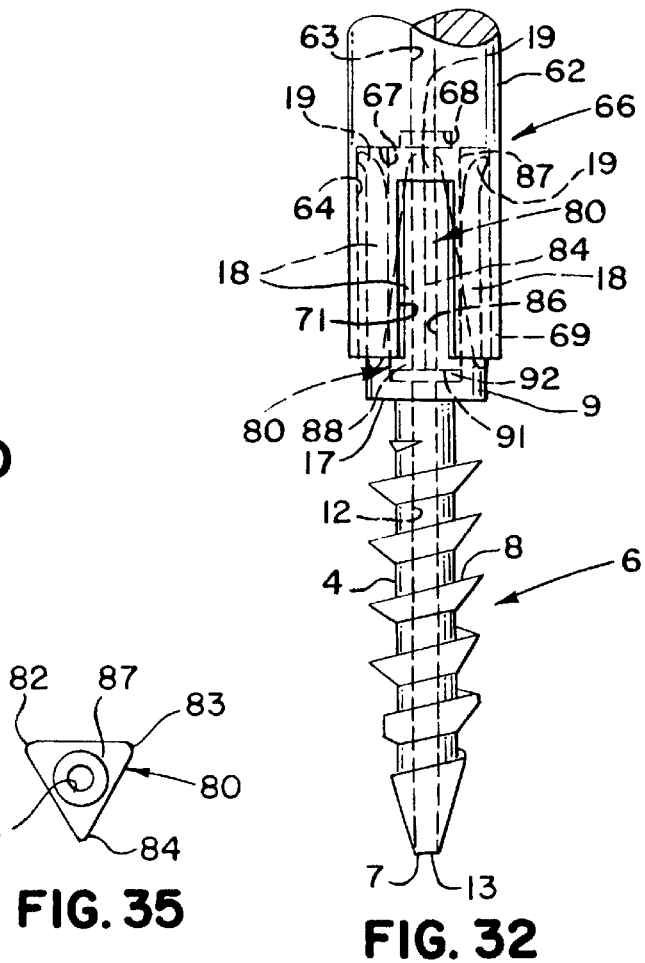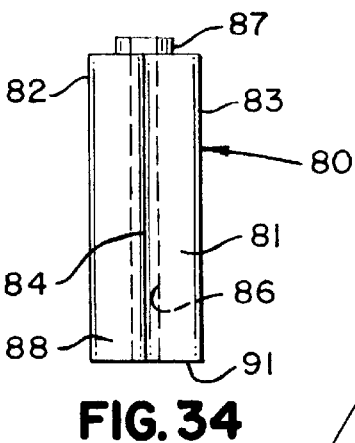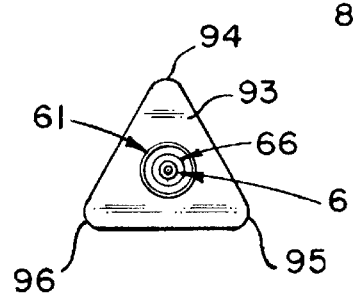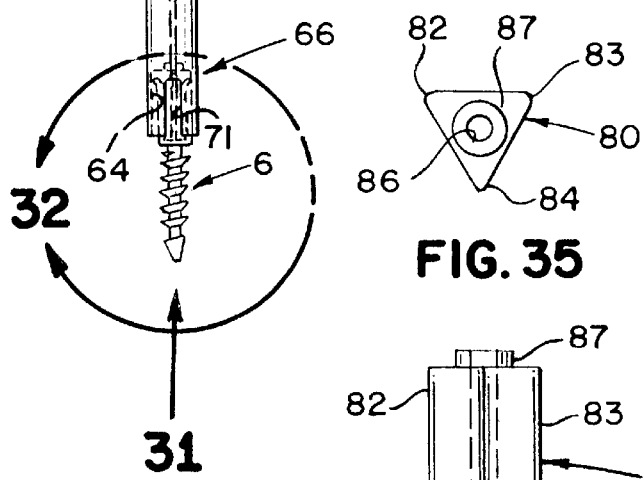
FIG. 30
FIG. 32
FIG. 35
FIG. 34
FIG. 31
FIG. 33

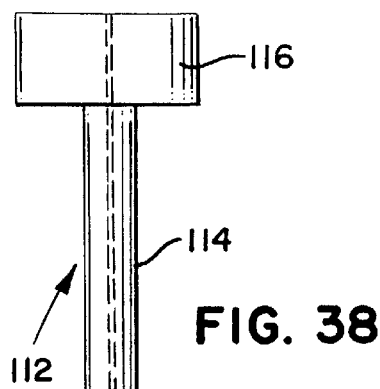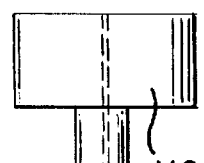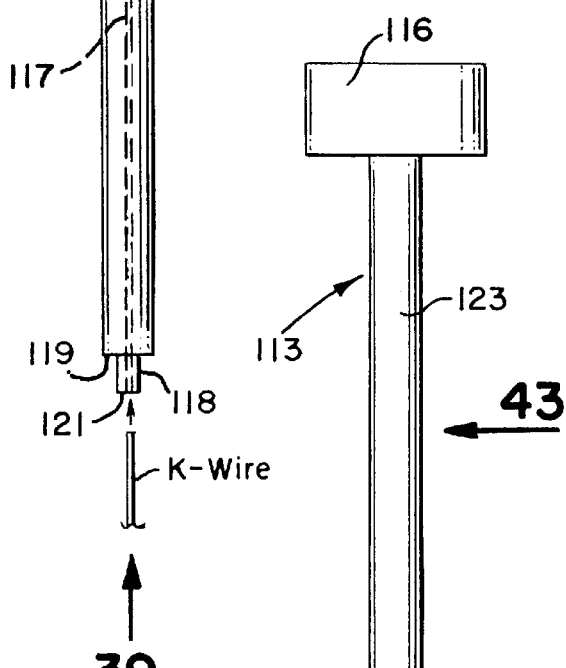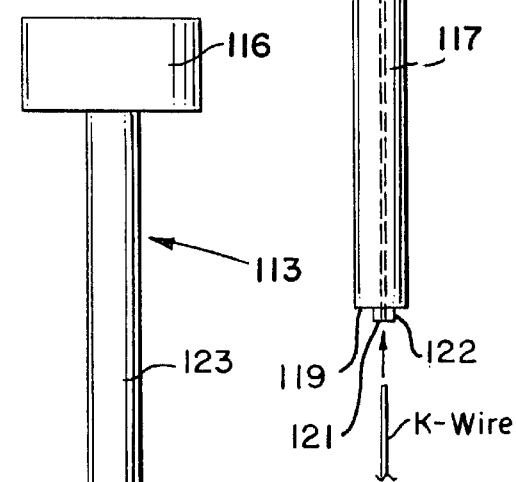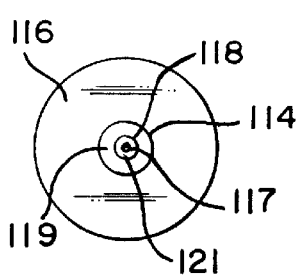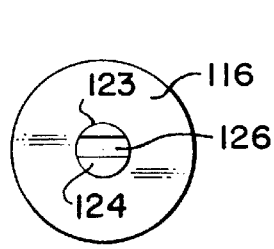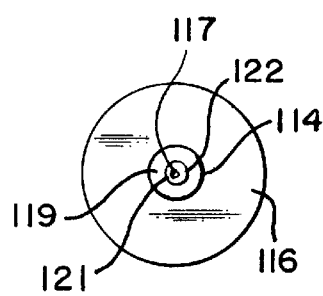

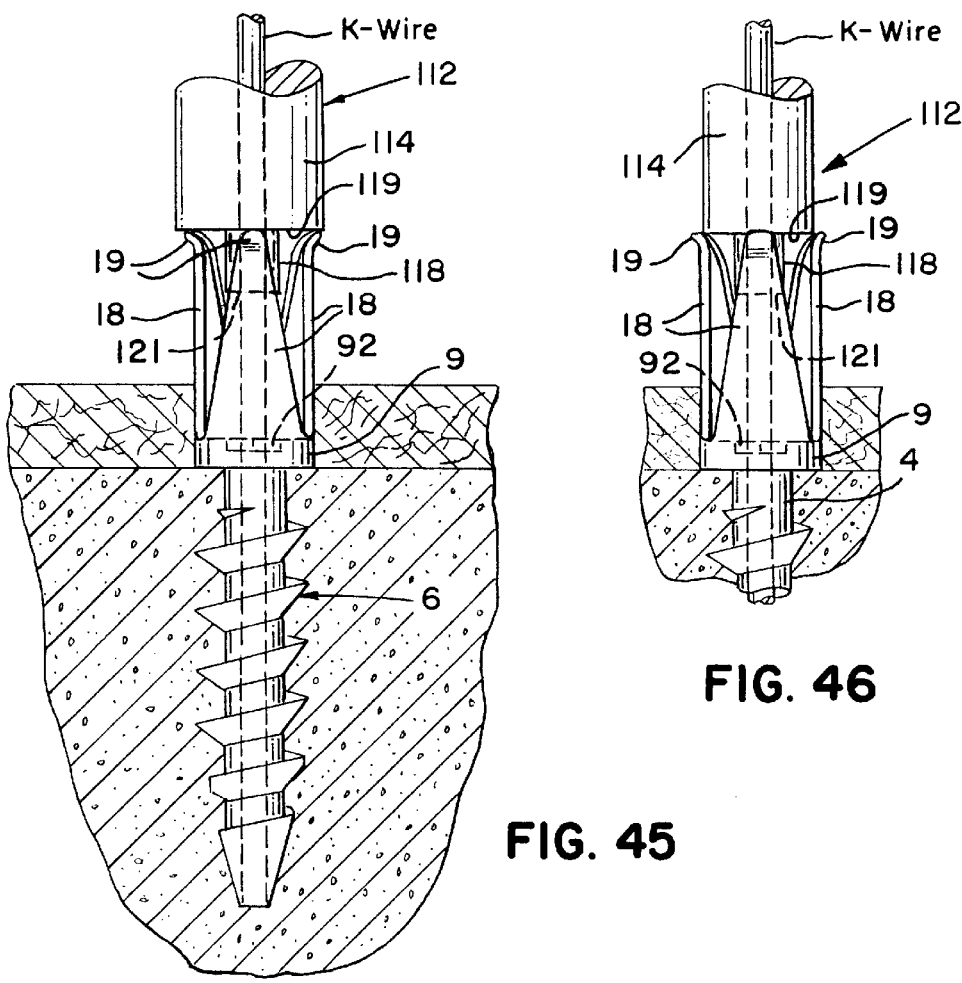
FIG. 45
FIG. 46
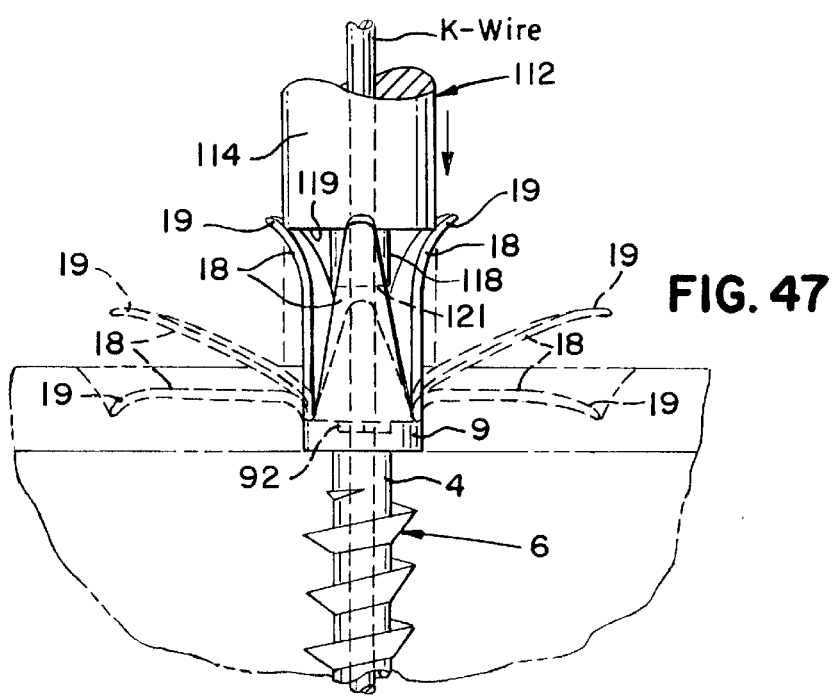
FIG. 47

५,८४०,०७८

METHOD AND APPARATUS FOR MECHANICAL ATTACHMENT OF SOFT TISSUE TO BONE TISSUE

BACKGROUND OF THE INVENTION

1. Field of the Invention

This invention relates to a method and apparatus for mechanically retaining soft tissue in intimate contact with bone tissue, and more particularly, in one aspect, relates to a metal rivet including an anchor portion adapted to be anchored in bone tissue and having an integral head portion reformable to clamp soft tissue intimately to the bone tissue, and which, in another aspect, relates to the instruments and method of placing the rivet and thereafter in situ permanently reforming the rivet head to form a metallic clamp for soft tissue.

2. Description of the the Prior Art

A preliminary patentability and novelty search has disclosed existence of the United States patents listed below.

| 4,963,144 | 5,013,316<br>5,102,421 | 5,037,422 |
|---|---|---|

Briefly, U.S. Pat. No. 4,963,144 discloses a bone screw for re-attachment of a small fragment of bone that has become separated from a larger bone mass, such as, for example, a small fragment of bone that has become separated from a femoral condyle. There has not been found in this patent a teaching of the concept of mechanical attachment of a mass of soft tissue to an associated bone mass.

U.S. Pat. No. 5,013,316, unlike the patent previously discussed, does disclose the concept of attachment of a mass of live soft tissue to an associated bone mass, but the structure for effecting such attachment and the method utilized differ significantly from the structure and method of the instant invention. U.S. Pat. No. 5,013,316 discloses a soft tissue anchor system including a hollow bone screw having a hexagonal interior periphery for mating with a complementary configured driver to enable turning the bone screw into a bone. Internally, the hollow bone screw is undercut to provide shoulders against which the tapered conical head of a tack locks itself after being driven through the mass of soft tissue and into the screw. At its opposite end, the soft tissue tack is provided with a plurality of circumferentially spaced spikes that penetrate a ligament or tendon, thus securing it to the surface of the underlying bone. The concept of in situ formation of the soft tissue clamping means has not been found in this patent.

U.S. Pat. Nos. 5,037,422 and 5,102,421 both disclose the placement of an anchor in bone, but do so for the attachment of sutures thereto, which sutures, in turn, are threaded through the mass of soft tissue to retain it against the bone mass in which the anchor is embedded. In situ formation of the anchor means does not appear to be disclosed by these patents.

Additional United States patents that are known to exist include the following:

| 4,872,451 | 4,976,715<br>5,203,784 | 4,988,351 |
|---|---|---|

U.S. Pat. No. 4,872,451 discloses a ligament repair kit and procedure for installing a cannulated bone screw and ligament washer to retain ligament tissue at a selected bone site. The tissue retention means includes both a screw and a washer, and does not appear to disclose the concept or structure of an in situ reformable rivet as in the invention disclosed and claimed herein.

U.S. Pat. No. 4,976,715 discloses a biodegradable repair tack that performs the same function as biodegradable sutures conventionally employed in meniscal and other surgical repair of soft tissue. Again, there is nothing disclosed in this patent to suggest the use of a metallic in situ reformable rivet of the type disclosed herein. U.S. Pat. Nos. 4,895,148 and 4,924,865 are by the same joint inventors and relate, respectively, to the method of utilizing a biodegradable tack structure for joining torn parts of bodily tissue, and to a biodegradable tack per se, again being devoid of a teaching of a metallic in situ reformable soft tissue clamping means.

U.S. Pat. No. 4,988,351 discloses a soft tissue washer having spikes and apertures that enable soft tissue to flow into and bind itself to the washer, and which provides a proximally recessed central aperture to receive a low profile screw adapted to be threadably engaged with an underlying bone mass, thus enabling retention of soft tissue in contact with an attachment site on the bone mass. Neither the concept nor the structure of an in situ reformable rivet as disclosed herein is taught by this patent.

U.S. Pat. No. 5,203,784 discloses a bioabsorbable tack structure that includes annular ribs spaced along a cannulated shaft that is impact-driven through soft tissue and into bone tissue to retain the soft tissue secured to the bone. As with the previously discussed patents, nothing has been found in this patent that suggests an in situ reformable metallic rivet structure normally intended to remain permanently in the patient, and which includes a portion that is reformable after anchoring of the rivet in an associated bone mass whereby to clamp soft tissue to the bone mass.

U.S. Pat. Nos. 4,884,572 and 5,129,906 disclose tacks for treating torn bodily material in vivo, and apparatus for deploying their respective tacks. Both tacks are formed from biodegradable material, and both are deployed by the application of an axially directed force to drive the tack into the tissue. Neither patent discloses a structure that utilizes rotation for implantation, and neither patent discloses a structure embodying an in situ reformable means for clamping tissue to bone following placement of the anchor in bone tissue.

An analysis of the prior art indicates that the most prevalent method and means for stabilizing soft tissue, with or without the use of an anchor embedded in bone tissue, is through the use of sutures. The following patents exemplify this method, and the various means for deploying sutures.

| 4,632,100 | 4,898,156 | 4,899,743 |
|---|---|---|
| 4,968,315 | 5,002,550 | 5,078,730 |
| 5,084,058 | 5,087,263 | 5,133,723 |
| 5,141,520 | 5,174,087 | 5,207,679 |
| | 5,217,486 | |

In open surgery a large incision is usually required to gain adequate access to a surgical site, causing increased trauma to the patient, long periods of immobilization and, as a consequence, long periods of rehabilitation and recovery. The disadvantages of open surgery are particularly troublesome in joint surgery, or arthrotomies, and more particularly in re-attaching torn or severed soft tissue, such as ligaments, tendons or muscles, to bone on or about an articulable joint.

As seen from the prior art first above noted, some effort has been expended to devise ways and means to re-attach separated "soft" tissue to bone tissue without the use of sutures. U.S. Pat. No. 4,988,351 teaches a variety of configurations of washers in conjunction with a cancellous bone screw to exemplify this effort. One disadvantage of these early efforts is the diametric size of the washers required to stabilize and retain the soft tissue in intimate contact with bone tissue, and the size of the incision required for placement of such washers. Advances in arthroscopic surgery, both in technique and instrumentation, have minimized the size of the incision or portal through which arthroscopic surgery is performed.

Advances in fastening devices in the recent past designed for use during arthroscopic surgery are typically of two types. The first type is similar to a tack with a small diameter head (generally around 4 mm diameter) which can be inserted through the separated soft tissue for retention purposes. This type of tack is exemplified in U.S. Pat. No. 4,976,715. As shown in the patent, a variety of ridges and barbs are utilized to retain the tack embedded in the tissue into which it is inserted.

The second type of fastening device is an anchor member adapted to be embedded in bone tissue, and used to secure one or more sutures, which are then utilized to tie the separated soft tissue to a bone site for eventual regeneration and re-attachment thereto. The various types of anchors, and the arthroscopic instrumentation for their placement in a bone mass are represented in the prior art patents noted above, including U.S. Pat. No. 4,968,315. As there seen, threads, barbs and ridges are utilized for fixation of the anchor member in the bone mass. Since this type anchor dictates the use of sutures, it is disadvantageous during arthroscopic surgery for the reason that it requires excessive manipulation through a very small incision, thus increasing the difficulty and the time consumed to accomplish the surgery. Additionally, it is sometimes necessary to utilize additional incisions and additional anchors and sutures to secure the soft tissue to the bone mass.

While history, as exemplified by the patents noted above, indicates the prevalence in the past of the use of sutures for fixation purposes of soft tissue, to bone or otherwise, it is clear that since the advent of arthroscopy, fixation of tendon or ligament tissue to bone for restoration of function and/or joint stability through use of anchors fixed in a selected site in a bone mass and to which site the tendon or ligament is intimately clamped without the use of sutures, is becoming a much more effective technique, especially with the acceleration of development of arthroscopic methods and means for fixation.

Accordingly, it is one of the important objects of the present invention to overcome the disadvantages of the prior art by providing a method and apparatus for mechanical attachment of soft tissue to bone in vivo with a unitary rivet and without the use of sutures.

Another object of the invention is the provision of a method and apparatus for securing torn or severed tissue to bone tissue with minimal manipulation and in minimal time.

A still further object of the invention is the provision of a method and apparatus for securing torn or severed tissue to bone tissue through use of arthroscopic surgery techniques to minimize the size of the access portal through which a bone site is exposed, to which site soft tissue to be attached is mobilized, and through which soft tissue a rivet having an in situ reformable head is inserted and anchored in the bone site, whereupon the rivet head is reformed in situ to clamp the soft tissue to the bone site.

A still further object of the invention is the provision of a cannulated metallic rivet having an anchor portion including an inner periphery symmetrical about a longitudinal axis and an axially extending integral head portion including a plurality of circumferentially spaced parallel lugs susceptible of in situ reformation to project radially outwardly in relation to the longitudinal axis of the rivet.

Yet another object of the invention is the provision of a cannulated metallic rivet symmetrical about a longitudinal axis and including an exteriorly threaded anchor portion and an axially extending head portion including a plurality of circumferentially spaced lugs susceptible of in situ reformation into a common plane perpendicular to the longitudinal axis.

Yet another object of the invention is the provision of arthroscopic instrumentation including a soft tissue positioning instrument with locator means, a soft tissue positioning instrument without locator means, a cannulated drill guide, a rivet insertion instrument, and multiple instruments, each useful to effect a different degree of reformation of the rivet head.

Another object of the invention is the provision of a rivet for securing soft tissue to a bone mass wherein the rivet constitutes a unitary structure of a first configuration symmetrical about a longitudinal axis prior to implantation and reformable in situ following implantation to reform a portion of the rivet to a second configuration in which soft tissue is clamped between the reformed portion of the rivet and the bone mass.

The invention possesses other objects and features of advantage, some of which, with the foregoing, will be apparent from the following description and the drawings. It is to be understood however that the invention is not limited to the embodiment illustrated and described since it may be embodied in various forms within the scope of the appended claims.

SUMMARY OF THE INVENTION

In terms of broad inclusion, in one aspect, the invention comprises a metallic cannulated rivet particularly adapted for implantation in a bone mass through use of arthroscopic or open surgery utilizing, in either case, a minimally sized portal or incision to locate and prepare the bone site for attachment of soft tissue thereto, and the implantation in the bone site of a first configuration of the rivet, following which a portion of the rivet projecting from the bone site and penetrating the soft tissue is reformed in situ to clamp the soft tissue to the bone site. In a second aspect, the invention comprises the method and instrumentalities for effecting implantation of the rivet and reformation thereof in situ to mechanically clamp the soft tissue to the bone site. Regarding the method of implantation, a portal or incision is formed to expose and prepare the bone site, torn or severed soft tissue is mobilized to intimately contact the bone site, the soft tissue is retained in proper position and a K-wire is advanced through the portal to penetrate the soft tissue and the bone mass to a predetermined depth and mark the point of implantation of the cannulated rivet. Thereafter, the rivet in its first configuration is advanced along the K-wire and inserted through the formed aperture in the soft tissue and anchored in the bone mass at the bone site with its proximate end projecting above the soft tissue. The head of the rivet is next reformed to clamp the soft tissue to the bone site, and the portal is closed.

BRIEF DESCRIPTION OF THE DRAWINGS

FIG. 16 is a side elevational view of a tissue positioning instrument but without the locator lug as illustrated in FIG. 12.

FIG. 17 is a right side elevational view of the instrument illustrated in FIG. 16, taken in the direction of arrow 17.

FIG. 18 is a top plan view of the instrument of FIG. 16.

FIG. 19 is a bottom plan view of the instrument of FIG. 17.

FIG. 23 is a side elevational view showing the operative telescoped and interlocked combination of the tissue positioning instrument and the cannulated drill guide, portions of the structure being broken away to reveal underlying structure.

FIG. 24 is a right side elevational view of the assembly illustrated in FIG. 23, in the direction of arrow 24, portions of the structure being broken away to reveal underlying structure.

FIG. 25 is a top plan view of the assembly taken in the direction of the arrow 25 in FIG. 24.

FIG. 30 is a view similar to FIG. 26 but showing the insertion tool with a rivet mounted thereon.

FIG. 31 is a bottom plan view of the rivet insertion instrument illustrating the distal end of the instrument with a rivet mounted on the distal end of the insertion instrument.

FIG. 32 is a fragmentary enlarged elevational view partly broken away of the distal end of the rivet insertion instrument defined by the arrowed circle 32 in FIG. 30, and illustrating a rivet mounted in the instrument.

FIG. 33 is a bottom plan view of a prtially completed insertion instrument, illustrating the distal end of the instrument after formation of the rivet-retaining skirt portion but prior to assembly thereon of the rivet-rotating driver member.

FIG. 34 is an elevational view of the triangularly configured rivet-rotating driver apart from other structure.

FIG. 35 is an end elevational view of the rivet-rotating driver illustrated in FIG. 34.

FIG. 38 is a side elevational view of a rivet lug-reforming instrument for use in commencing the lug reformation process in situ after the rivet is threaded into the bone at the bone site.

FIG. 39 is a bottom plan view of the rivet lug-reforming instrument of FIG. 38.

FIG. 40 is a side elevational view of a second or modified rivet lug-reforming instrument similar to the FIG. 38 instrument but with a shorter limit head projecting from the distal end.

FIG. 41 is a bottom plan view of the rivet lug-reforming instrument of FIG. 40.

FIG. 42 is a side elevational view of a third rivet lug-reforming instrument formed with a slot in its distal end for individual engagement with the laterally projecting lugs after the K-wire has been withdrawn.

FIG. 43 is a view of the rivet lug-reforming instrument of FIG. 42 taken in the direction of the arrow 43 in FIG. 42.

FIG. 44 is a bottom plan view of the distal end of the rivet lug-reforming instrument of FIG. 42.

FIG. 45 is a fragmentary side elevational view illustrating the initial relationship of the lug-reforming instrument of FIG. 38 with the associated ends of the lugs prior to the first impact delivered to the reforming instrument by the surgeon's mallet.

FIG. 46 is a fragmentary side elevational view illustrating the initial relationship of a slightly modified lug-reforming instrument with the associated ends of the lugs prior to the first impact delivered to the reforming instrument by the surgeon's mallet.

FIG. 47 is a fragmentary view illustrating the lug-spreading camming effect on the soft tissue clamping lugs when the reforming tool is driven progressively further between the lugs toward the root portions thereof.

DESCRIPTION OF THE PREFERRED EMBODIMENTS

In terms of greater detail, the method and apparatus of the invention relates to mechanically clamping soft tissue to a prepared bone site through use of a metallic rivet of initial minimal diametric dimension adapted for insertion through a minimal incision or portal, and inserted through soft tissue for implantation in the underlying bone in that minimal dimension configuration and subsequently, in situ, reformed to provide a larger diameter proximal aspect to clamp soft tissue to the bone.

It is believed that the method and apparatus will be best understood by first describing the reformable rivet per se, then the instrumentalities utilized by the surgeon for embedding the reformable rivet in a bone mass in association with soft tissue, and ultimately explaining the method or procedures for in vivo reformation of the rivet. Some of the methods and procedures will of course become apparent as a result of the description of the rivet per se and the instrumentalities for its placement. In the interest of brevity in this description, conventionally known surgical techniques and practices relating to establishing an aseptic or sterile surgical environment are believed to be common knowledge in the medical profession and are therefore purposely not included in this description.

Figure 1:
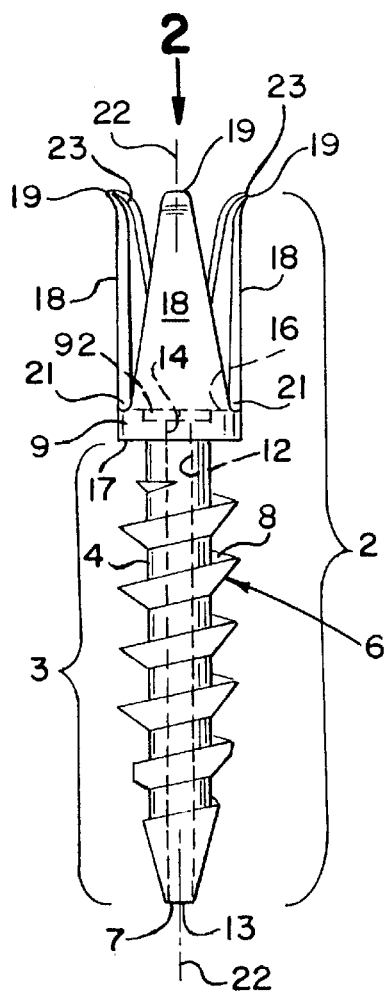
FIG. 1 is a side elevational view of the rivet in its first or initial configuration prior to implantation in a bone mass.

Referring to FIG. 1, it will be seen that the rivet per se as an article of manufacture and sale and in its initial or first configuration prior to implantation and reformation is designated generally by the numeral 2, and includes a tubular shank portion 3 having an outer periphery 4 about which is formed a spiral screw thread designated generally by the numeral 6. The thread commences at the distal end 7 of the shank and progresses in appropriately spaced buttress-type spiral lands 8 along the shank, terminating adjacent a cylindrical head portion 9 integral with the shank and having an outer diameter substantially the same as the majority of the lands forming the spiral thread. Extending through the shank and the head portion 9 is a central passageway or bore 12, converging at the distal end of the shank with the lower diminished-diameter land and providing an opening 13 in the distal end of the shank, and at its proximal end providing an opening 14 in the upper or anterior surface 16 of head 9.

Figure 2:
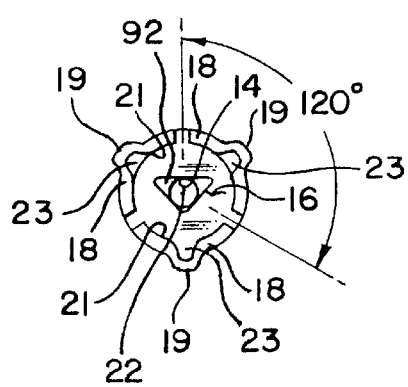
FIG. 2 is a top plan view of the rivet shown in FIG. 1.

It should be noted that the lower or posterior surface 17 of the head portion is parallel with the upper or anterior surface 16 of the head portion. Projecting from the anterior surface 16 of the head portion are a plurality of integral circumferentially spaced axially extending lugs 18, shown in FIG. 1 to be generally tapered toward their free ends 19 which are thus spaced apart a greater distance than the root portions 21 of the lugs where they integrally join the surface 16 in relatively closely spaced relationship as shown. The bodies of the lugs are generally arcuate in cross-section (FIG. 2), and symmetrically spaced about a central longitudinal axis 22. At their free ends 19, the lugs are rounded and flared radially outwardly to provide inner cam surfaces 23 for a purpose which will hereinafter be explained.

Figure 3:
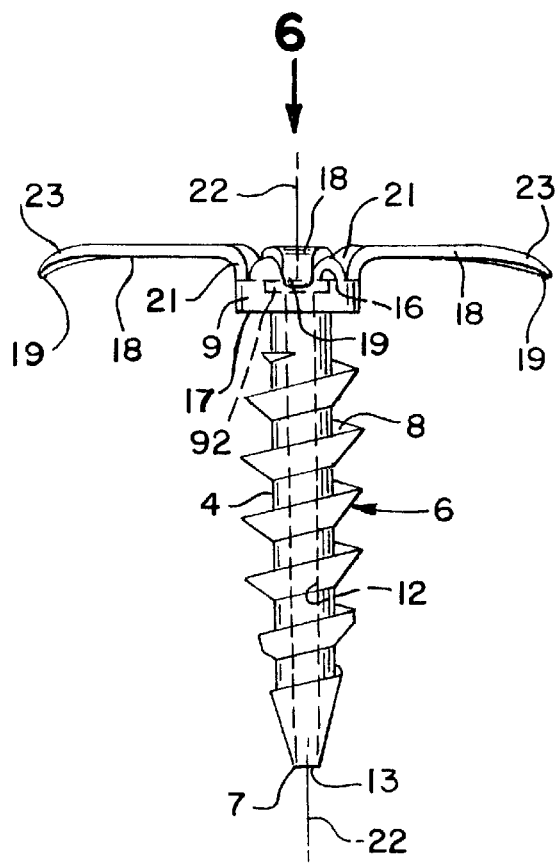
FIG. 3 is a side elevational view of the rivet in its second or ultimate reformed soft tissue clamping configuration but shown apart from soft tissue and bone in the interest of clarity.
Figure 6:
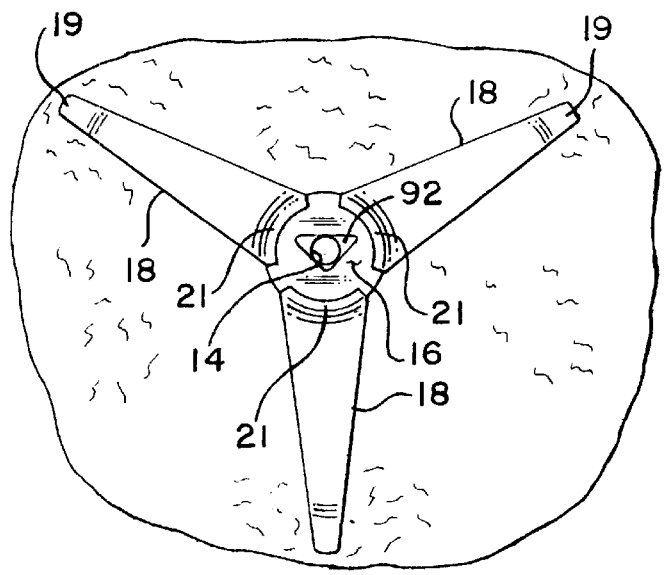
FIG. 6 is a fragmentary plan view of the implanted and reformed rivet showing the spread of the clamping lugs overlying the soft tissue and clamping it to the bone at the soft tissue attachment site.
Figure 9:
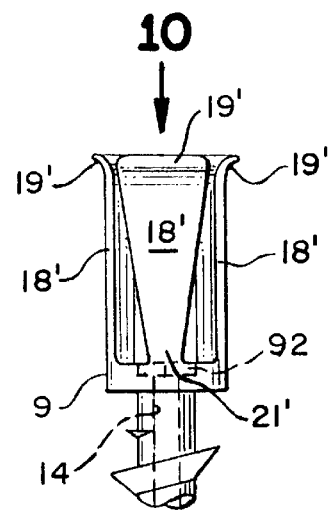
FIG. 9 is a fragmentary side elevational view illustrating the reformable head of the rivet with soft tissue clamping lugs modified in their configuration to minimize the arcuate width of each lug at its root and maximize its width at its free end.
Figure 10:
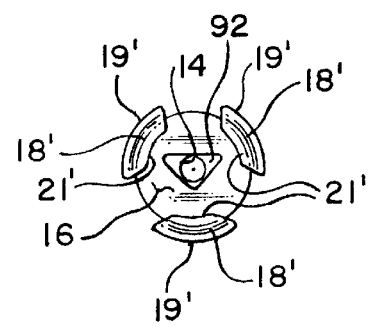
FIG. 10 is a top plan view of the FIG. 9 rivet structure.
Figure 11:
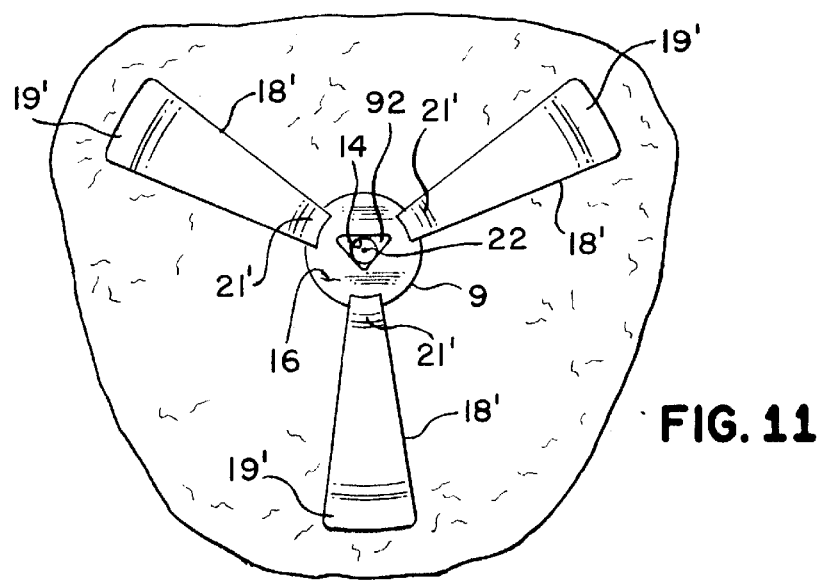
FIG. 11 is a top plan view of the modified structure of FIG. 9 illustrating the configuration of the lugs in relation to the shank portion of the rivet after reformation of the lugs into soft tissue clamping orientation, shown apart from soft tissue.
Figure 12:
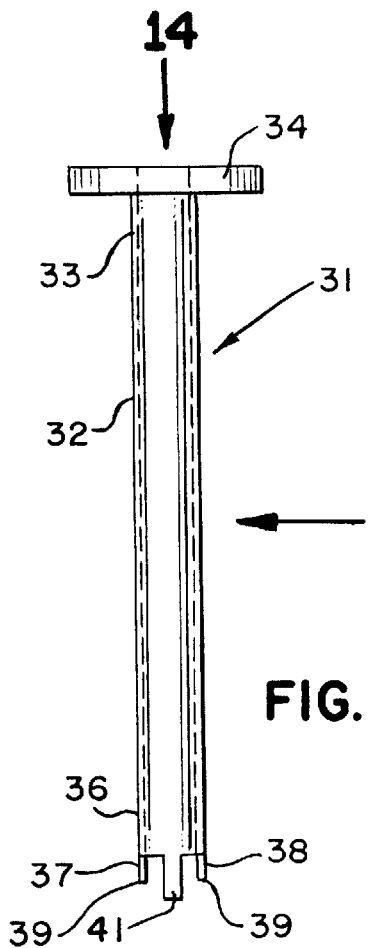
FIG. 12 is a side elevational view of a soft tissue positioning instrument equipped with a locator lug.
Figure 13:
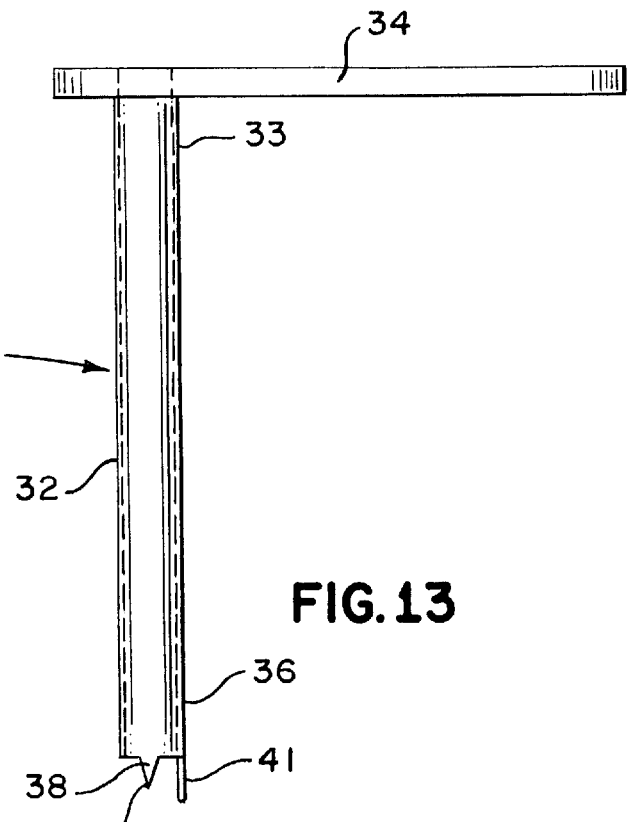
FIG. 13 is a side elevational view of the soft tissue positioning instrument of FIG. 13 taken in the direction of the arrow 13 in FIG. 12.
Figure 14:
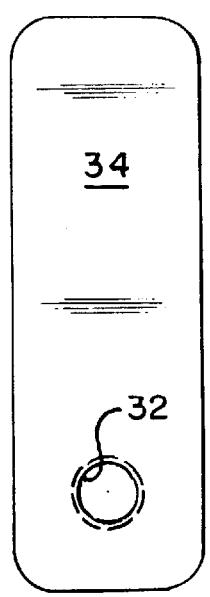
FIG. 14 is a top plan view of the positioning instrument illustrated in FIG. 12.
Figure 15:
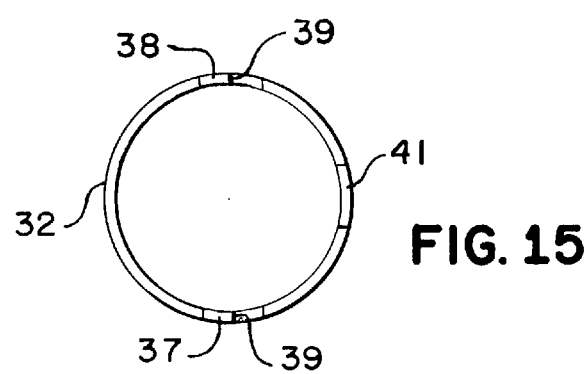
FIG. 15 is a bottom plan view of the positioning instrument illustrated in FIG. 13.

It will be understood that because the arcuate root portion 21 of each lug possesses a longer arcuate expanse than the free end of the lug, the lugs in this configuration are more resistant to both intentional reformation into the planar disposition illustrated in FIG. 3, and to unintentional reformation out of the planar disposition shown. This quality is very useful where use of the rivet requires the rivet to withstand strong axially directed tensive forces exerted by soft tissue that has been clamped to a bone mass. However, it should also be understood that in some applications, such major strength characteristics of the lugs are not required. Thus, where the forces applied to the rivet by soft tissue are mainly transverse to the longitudinal axis of the rivet, the lugs 18' may, alternatively, take the form illustrated in FIGS. 9, 10 and 11, to provide a narrower root portion 21' where the lugs join the head portion of the rivet, thus diminishing the amount of force required to initially reform the lugs into the planar disposition shown in FIG. 11, while still retaining sufficient strength to securely clamp soft tissue to an associated bone mass and to withstand the degree of transverse forces applied to the rivet by soft tissue, as by the tensioning of a tendon or ligament. An added advantage of utilizing a narrower root 21' where each lug joins the head portion is the facility with which the narrower root portion of the lug may be severed in the event it is necessary to remove the rivet in a subsequent surgical procedure, or the facility with which the lugs may be reformed into a minimal diameter circular array as shown in FIG. 10, i.e., returned to their initial disposition, thus enabling the rivet to be rotated (unscrewed) and removed through a minimally sized portal no larger than the one by which the rivet was initially implanted. While it is contemplated that because the rivet is formed from surgical grade stainless steel it may remain embedded in the bone mass indefinitely, nevertheless, in some instances, it may be necessary or expedient to remove the rivet, and the narrow lug roots 21' afford that opportunity either through severance or reformation.

Figure 7:
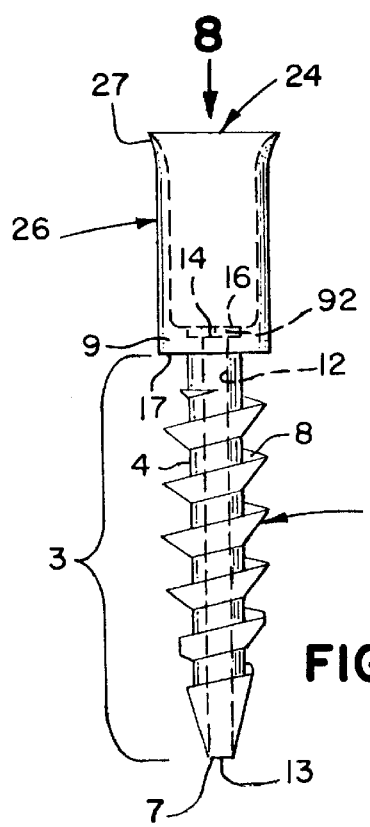
FIG. 7 is a side elevational view of a partially fabricated rivet, illustrating the cylindrical tubular head portion extending integrally from the threaded shank or anchor portion of the rivet prior to formation of the soft tissue clamping lugs.

Referring to FIG. 7, one of the ways, among others, in which the rivet may be fabricated is to start with a medical grade stainless steel cylindrical rod having a diameter of 4.0 mm, for instance, and a length of about 14.0 mm. Obviously, different dimensions may be utilized to fabricate different size rivets for different applications, where the environment of application or implantation determines the size rivet that should be used. Through use of appropriate machinery, the elongated bore 12 is formed in the rod, a spiral thread 6 is formed on the outer periphery of the shank portion of the rod, and a cylindrical recess 24 is formed in the end of the rod by milling or otherwise to form the head 9 having a thickness of about 1.0 mm and from the anterior face 16 of which extends an integral tubular cylindrical head portion 26. Through an appropriate metal spinning technique, the tubular cylindrical head portion 26 may be formed with a flared end portion 27 as illustrated prior to formation of the lugs. Alternatively, the ends of the lugs may be flared utilizing a forming die following formation of the lugs.

Formation of the lugs 18 proceeds through use of appropriate and well known conventional electric discharge machining (EDM) techniques applied to the tubular cylindrical head portion 26 to form separate "petals" or lugs 18 that are equally spaced 120 degrees circumferentially about the anterior face of the head in the form illustrated in FIGS. 1, 2, 9 and 10.

It should be understood that while I have shown a formation of only three lugs, more or less may be formed, depending upon the end usage of the rivet. The formation of the lugs through use of electric discharge machining enables precise and clean definition of the lugs which, in the embodiment illustrated in FIGS. 1 and 9, are formed with a length of about 7 mm measured from the anterior face 16 of the head 9, and having a thickness of only about 0.40 mm. In the interest of providing more easily visualized size characteristics, the overall length of the rivet in decimal fractions of an inch is equal to about 0.874 inch, the diameter of the cylindrical head member 26 is equal to about 0.159 inch, while the length of the lugs is only about 0.278 inch. It is not intended that the invention be restricted to these dimensions, since various sizes of rivets may be fabricated to fulfill the needs of various implantation environments.

While the rivet described above may be implanted utilizing open surgery procedures, and in some circumstances it may be required or expedient to do so, it is primarily intended that the rivet of this invention be implanted utilizing arthroscopic surgery. This form of surgery has been discussed at length in the prior art cited above. Some of its primary advantages are that it is less invasive of the patient's body, usually proceeds more rapidly, promotes faster healing, and thus enables a relatively prompt recovery for the patient. To accomplish successful re-attachment of soft tissue to bone through use of a metallic rivet such as the one described above and illustrated in the drawings, it is imperative that no metal appear in or be involved in the articular surface of any joint, since this will destroy the joint.

The description of technique and instrumentation that follows is applicable to the implantation of a metallic, namely, surgical grade stainless steel, soft tissue fixing rivet which has a sufficiently small degree of tissue clearance so that it will never involve abrasion or destruction of joint in which it is implanted, and will quite adequately secure all soft tissue to its prepared bony bed until scar formation and adhesion through natural processes has occurred.

Whether it is accomplished arthroscopically or by open surgery, the area of tendon or ligament avulsion is exposed and prepared by the use of some type of burr to decorticate the area of attachment, thus exposing the raw cancellous bone. This procedure will ensure an adequate blood supply and scar tissue formation to achieve proper and natural fixation (grafting) of the tendon or ligamentous structure to the bone.

When tendon or ligament avulsion occurs, the soft tissue tendon or ligament tends to pull away from or recede from the location from which it was torn. To re-attach the tendon or ligament, it is necessary to mobilize the soft tissue from its detached location and relocate it on the prepared bone site. To effect this repositioning, I provide the soft tissue repositioning instruments illustrated in FIGS. 12–19, and, depending upon circumstances, may use one or the other or both of the two instruments shown. Referring specifically to the instrument illustrated in FIGS. 12–15, the soft tissue positioning instrument there shown is designated generally by the numeral 31, and is fabricated conveniently from 17-4 stainless steel, and includes an elongated tubular body portion 32 having an overall length of about 3.5 inches, an outside diameter of about 7 mm and an inside diameter of about 6.5 mm, thus resulting in a wall thickness of about 0.010 of an inch. At one end 33 the tubular body is rigidly fixed to a handle 34 that extends perpendicular to the longitudinal axis of the tubular body. As shown, the handle is defined by opposite long edges intercepted by end edges, and includes top and bottom surfaces, with the connection between the tubular body and the handle being effected adjacent one end of the handle, thus providing a convenient length for grasping by the surgeon and a lever for manipulation of the instrument as will hereinafter be described.

At its opposite end 36 remote from the handle 34, the tubular body is provided with a pair of diametrically opposed tissue positioning lugs 37 and 38, each lug preferably being formed integrally as an extension of the tubular wall, and shaped in the form of an isosceles triangle having a sharpened apex 39 as shown. Also formed integrally on the end 36 of the tubular body medianly between the lugs 37 and 38, is a joint locator lug 41 having a flat end edge 42 and parallel side edges 43 and 44 which, with the end edge 42, define the arcuate configuration of the locator lug 41 which, as shown, is somewhat longer than the lugs 37 and 38. I have found that an adequate length for the lugs 37 and 38 is about 0.157 of an inch, while the lug 41 may conveniently have a length of about 0.236 of an inch.

The tissue repositioning instrument is inserted into the incision or portal formed by the surgeon, and the lugs 37 and 38 are caused to impale the dislocated mass of soft tissue and by appropriate manipulation of the instrument, both laterally and pivotally about its own longitudinal axis, the mass of soft tissue is mobilized to return it to the prepared or conditioned bone site to which it is to be re-attached. The locator lug 41 is useful in this procedure by forming a guide or reference plane with respect to the joint between two relatively articulable bone masses to ensure that the rivet, when implanted, does not penetrate into the joint. Stated in other words, in the case of dislocating shoulder reconstruction, for instance, the soft tissue positioning instrument is manipulated so that the locater lug 41 rests on the articular surface of the joint. This will place the position of the rivet sufficiently below, i.e., spaced from, the articular surface so that no interference with articular cartilage can occur. The locator lug thus functions to properly position the impaled end of the instrument and the soft tissue in which it is impaled in relation to the joint to thus ensure proper placement of the rivet. Such mobility of the instrument and the soft tissue is facilitated by the perpendicular projection of the handle because it enables incremental repositioning of the soft tissue mass until it is in proper position for permanent adherence.

There are of course occasions when it is not necessary that the tissue positioning instrument be equipped with a locator lug 41. This will be the case where there is no joint and therefore no articular surface involved in the procedure and all that is necessary is that the soft tissue torn from its anchorage site be mobilized back to the prepared bone site for re-attachment. To fulfill this need, reference is made to FIGS. 16–19 where there is shown a tissue positioning instrument that is devoid of the locator lug 41. With the exception of the omission of lug 41, all other aspects of the instrument illustrated in FIGS. 16–18 are identical to the instrument illustrated in FIGS. 12–15. Accordingly, in the interest of brevity of this description, the same reference numbers identifying the same elements of the instrument of FIGS. 12–15 are utilized in FIGS. 16–19, and the pertinent portions of the description of the instrument of FIGS. 12–15 are included hereat by reference.

Figure 20:
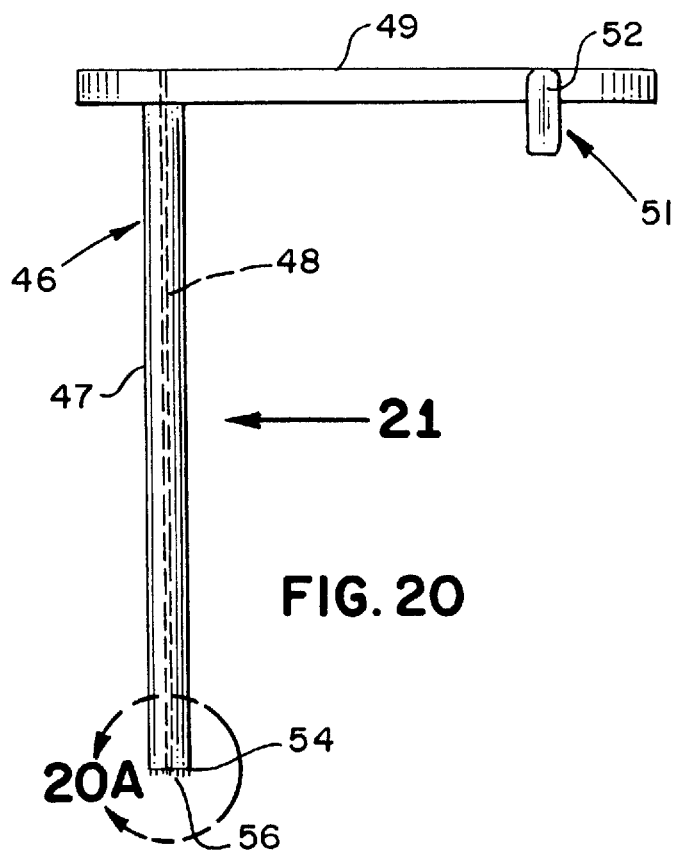
FIG. 20 is a side elevational view of a cannulated drill guide and tissue retention instrument incorporating a lock lug.
Figure 21:
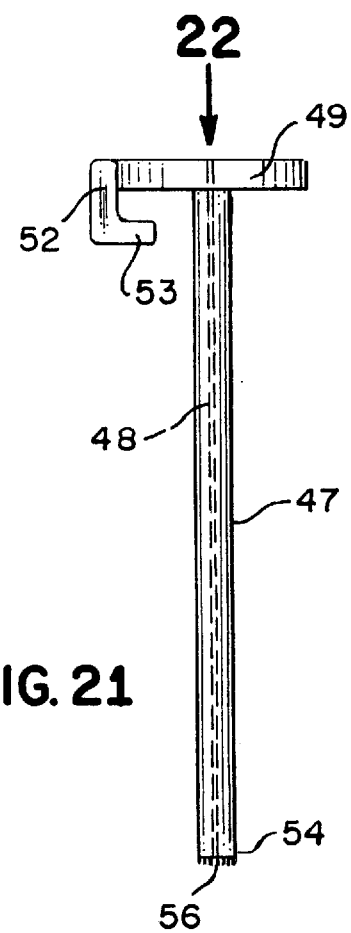
FIG. 21 is a right side elevational view of the cannulated drill guide and tissue retention instrument of FIG. 15.
Figure 20A:
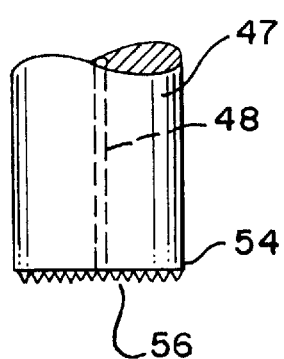
FIG. 20A is an enlarged fragmentary elevational view of the tissue-retention end portion indicated by the arrow 20A in FIG. 20.
Figure 22:
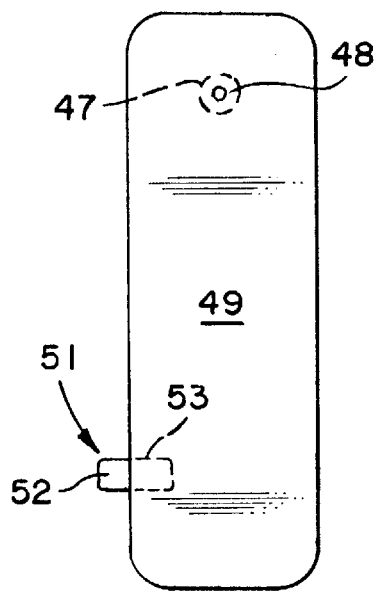
FIG. 22 is a top plan view of the cannulated drill guide, taken in the direction of the arrow 22 in FIG. 21.
Figure 28:
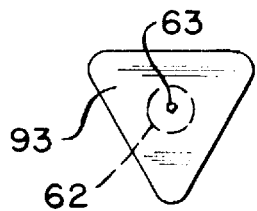
FIG. 28 is a top plan view of the rivet insertion instrument of FIG. 26, illustrating the triangular head thereof useful for indicating the orientation of the circumferentially spaced reformable tissue-clamping lugs of the rivet.

Thus, through manipulation of the soft tissue positioning instruments illustrated in FIGS. 12–19, having properly relocated the soft tissue mass to the prepared bone site to which it is to be permanently re-attached, a stainless steel drill guide instrument designated generally by the numeral 46 and illustrated in FIGS. 20–22 is provided and utilized to retain the now properly positioned soft tissue mass in proper position, and forms a sheath to guide insertion of a stainless steel K-wire, well known in the sugical profession, in a manner which will hereinafter be explained.

With the tissue positioning instrument 31 in tissue-impaling position as previously discussed, and with the mass of soft tissue having been mobilized to its proper or near proper position in relation to the prepared bone site, the drill guide sheath 46 is inserted telescopically through the tissue positioning instrument. The drill guide sheath includes an elongated tubular body 47 that possesses an outer diameter that forms a snug sliding fit with the interior of the tissue positioning instrument, thus enabling such telescoping insertion, and possesses a central bore 48 of about 0.035 of an inch. At one end the drill guide sheath is rigidly fixed to a handle 49 of the same size and configuration as the handle 34 of the tissue positioning instrument.

Additionally, the handle 49 of the drill guide sheath is provided with a lock means designated generally by the numeral 51, and including a lug portion 52 integral with one long edge of the handle 49 as shown, and a reentrant lug portion 53 that is spaced below the underside of the handle and which projects transversely inwardly from the edge to which the lug portion 52 is fixed. It will thus be seen, as illustrated in FIGS. 23–25, that when the drill guide sheath is telescopically engaged with the tissue positioning instrument, full penetration of the drill guide in the tubular body 32 of the tissue positioning instrument is achieved with the handles of the two instruments pivotally offset a sufficient amount for the reentrant lug portion 53 to clear the edge of the underlying handle 34 so that the underside of the drill guide handle comes to rest on the top side of the tissue positioning instrument handle 34. The two handles may now be pivoted relative to one another so that the reentrant lug portion 53 locks below the underside of the tissue positioning instrument handle 34. This prevents inadvertent axial displacement of the two telescopically related instruments, while enabling manipulation of the two as one to achieve and retain desired placement of the soft tissue mass in relation to the prepared bone site.

To further effectuate such proper placement, it should be noted that the end 54 of the drill guide sheath remote from the handle 49 is provided with serrated and sharp teeth 56 that penetrate the soft tissue surface, thus cooperating with the lugs 37 and 38 to precisely mobilize the mass of soft tissue to place it in proper position for re-attachment. When positioning and temporary retention of the soft tissue in relation to the prepared bone site has been achieved, a stainless steel K-wire of appropriate diameter and preferably having a sharp trocar point is slibably inserted into the bore 48 of the drill guide sheath, and advanced until the sharply pointed K-wire impales the soft tissue, passing therethrough, and penetrates the cancellous bone tissue to a depth sufficient that the mass of soft tissue will be held in position in relation to the underlying bone by the interaction of the K-wire and the tissue positioning instruments.

At this juncture in the procedure, the tissue positioning instrument, which now functions as a sheath for the drill guide instrument, is retained in position and the drill guide sheath instrument is withdrawn, leaving the stainless steel K-wire coaxially arranged within the tissue positioning instrument and in place to now function additionally as a guide wire for placement of the rivet. To effectuate this procedure, reference is made to FIGS. 26–32, wherein there is illustrated a rivet insertion instrument designated generally by the numeral 61. The insertion instrument 61 includes an elongated tubular body 62 symmetrical about a longitudinal axis and having an elongated axial bore 63 for reception of the K-wire so as to guide placement of the distal end of the insertion instrument, with a rivet mounted thereon, and guided by the K-wire and the circumscribing tissue positioning instrument, precisely at the previously selected prepared bone site for implantation of the rivet.

In the interest of clarifying dimensional proportions found to be satisfactory, the outside diameter of the tubular body 62 may conveniently be 0.236 inch, which equates to 6 mm, thus enabling the insertion instrument to slide down the K-wire in telescoping relationship with the tissue positioning instrument. Since the passageway or bore 63 is conveniently 0.035 inch, or stated another way, only 0.004 inch less than one (1) millimeter, it will be seen that the wall thickness of the tubular body 62 is about 2.979 mm, or just under 3 mm.

It is within the confines of these very small dimensions that a rivet-retaining socket 64 (FIGS. 27, 29, 32 and 33) is formed in the distal end 66 of the tubular body 62 to receive and detachably retain the three circumferentially spaced lugs 18. Since, as previously discussed, the outer limits of the flared ends of the lugs are coincident with a circle having a diameter of 5 mm, the socket 64 is formed to have an inside diameter of 0.193 inch. This dimension is approximately 0.0038 inch less than the 5 mm (0.19685 inch) spread of the free ends of the lugs.

Thus, to mount the rivet on the insertion instrument, the ends of the lugs are elastically constricted sufficiently, either digitally or with an appropriate tool, and then inserted into the socket and released, whereupon the lugs expand radially and impinge resiliently on the inner periphery of the socket, so that the outwardly directed resilient force exerted by the rivet lugs against the inside of the socket frictionally yet detachably retain the rivet within the socket against inadvertent axial displacement. After the rivet is set in the bone, all that is required to release the rivet is to tug slightly on the insertion instrument and pull the socket free from the ends of the lugs.

Again referring to FIGS. 27, 29, 32 and 33, it will be seen that the socket 64 is formed in the distal end of the tubular body 62 by appropriate machining, as by electric discharge machining or other appropriate method, to a depth of about 6 mm to form the recessed annular face 67 within which there is formed a smaller annular shoulder 68. Both the annular face 67 and the annular shoulder 68 are concentrically disposed with respect to the central bore or passageway 63. As illustrated in FIG. 33, the socket 64 is initially defined by a tubular cylindrical wall 69 concentrically disposed coaxially about the central axis of the tubular body.

In a subsequent machining operation, again conveniently by electric discharge machining or other appropriate method, the cylindrical wall 69 is provided with three slots 71, 72 and 73 (FIGS. 27 and 29) that are circumferentiall spaced at 120 degree intervals and that extend proximally along the distal end of the tubular body to a bottom limit 74 that is spaced below the annular face 67 sufficiently to provide a cylindrical lip 76 disposed between the bottom limit 74 of each slot and the annular face 67. The inner peripheries of the cylindrical lips are the surfaces against which the ends of the lugs 18 resiliently impinge when the temporarily resiliently constricted lugs 18 are inserted into the socket within the portion defined by the lips and then released. It will thus be seen that the rivet is detachably secured within the socket on the distal end of the insertion instrument and resiliently retained there against inadvertent axial displacement, while enabling intentional separation of the insertion instrument from the rivet once the rivet has been set in the bone. Each of the slots 71, 72 and 73 has an arcuate width equivalent to approximately 60 degrees, while the remaining wall portions 77, 78 and 79 also subtend an arc of approximately 60 degrees. Thus, when the rivet head is inserted into the socket, the rivet lugs, which are also spaced 120 degrees apart circumferentially, are oriented so that one of the slots is precisely located opposite one of the associated is lugs.

In addition to axial retention of the rivet on the insertion instrument, it is also preferable that the relationship between the insertion instrument and the rivet be such as to enable application of a rotational moment on the rivet by rotation of the insertion instrument so that the threads draw the rivet into the bone. To enable this mode of operation, and referring to FIGS. 27, 29, 34 and 35, in one embodiment, the insertion instrument is provided at its distal end and cooperatively associated with the socket 64 with a driver element designated generally by the numeral 80. As illustrated, the driver element comprises an elongated stainless steel member 81 having a triangular cross-section to provide apexes 82, 83 and 84, and is provided with an elongated centrally disposed bore or passageway 86 that corresponds in diameter with the passageway 63 in the tubular body 62 to enable passage of the K-wire. At one end, the triangular driver element is provided with an annular boss 87 dimensioned to form a tight press-fit and/or be silver brazed within the recess formed in the face 67 of the tubular body so that the end face of the annular boss 87 abuts the shoulder 68.

Figure 29:
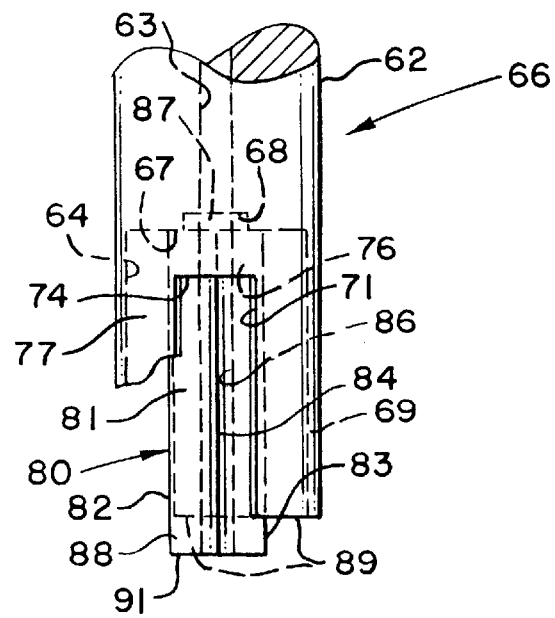
FIG. 29 is a fragmentary elevational view, greatly enlarged, and with a portion broken away for clarity, of the rivet retention end of the insertion instrument defined by the arrowed circle 29 in FIG. 26.
Figure 26:
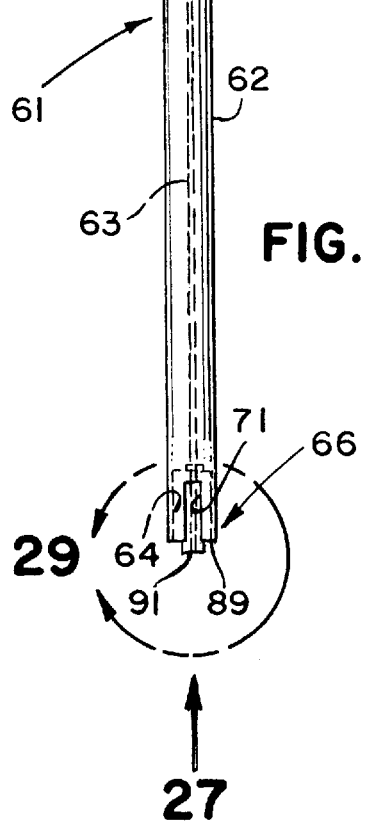
FIG. 26 is a side elevational view of a rivet insertion instrument, shown apart from a rivet.
Figure 27:
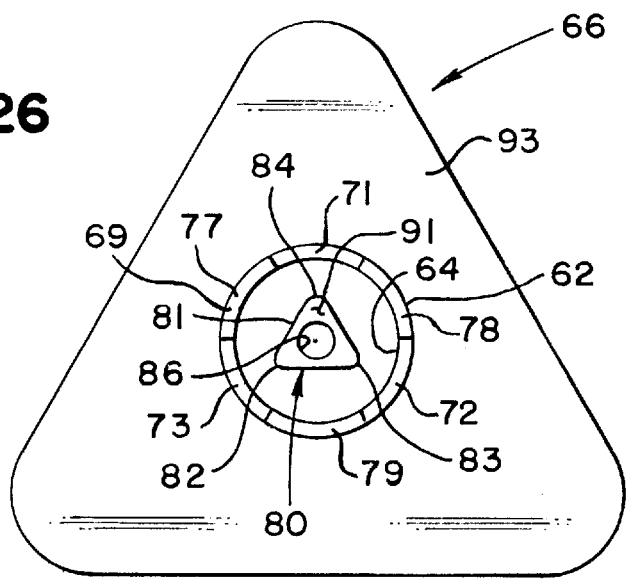
FIG. 27 is a bottom plan view of the insertion instrument illustrated in FIG. 26.

As illustrated in FIG. 29, the lower end portion 88 of the triangular driver element remote from the end thereof fixed to the annular face 67 of the tubular body projects below the lower or distal ends 89 of the arcuate socket wall portions 77, 78 and 79, and presents a flat face 91 that is sized to be snugly admitted into a correspondingly configured triangular recess 92 formed in the face 16 of the rivet head 9. Thus, the dimension A shown in FIG. 29 is calculated to enable the face 91 and the distal end portion of the driver element to drivingly engage the correspondingly configured recess 92 when the flared ends of the lugs 18 of the rivet extend into socket 64 to impinge resiliently against the arcuate wall portions 74, thus enabling imposition of a rotational moment on the rivet through rotation of the instrument while retaining the rivet against axial displacement. It is important to note, as illustrated in FIG. 27, that the apexes of the driver element coincide with the median planes of the associated slots when the rivet is inserted into the insertion instrument socket in preparation for implantation of the rivet.

At its proximal end remote from the socket 64, the tubular body 62 is rigidly fixed to a head member 93 that is triangular in configuration as shown to provide three apexes 94, 95 and 96 which correspond in circumferential placement with the three lugs 18. The head member functions to provide a handle by which the instrument and rivet may be digitally rotated to drive the rivet into the bone, and to provide both visual and tactile references to indicate the rotational position of the insertion instrument, and therefore the rotational position of the three lugs 18 on the rivet head. Alternatively, the head member may be cylindrical and provided circumferentially with indentations to provide finger grips to aid digital manipulation, and with an embossed or raised index mark or marks that are circumferentially aligned with one or more of the lugs 18 to thus indicate the spacial orientation of the lugs 18 with respect to the soft tissue mass they clamp to the bone site.

In the selectively detachable coaxially interengaging relationship between the rivet and the insertion instrument, at least three interrelated design conditions are particularly important. One is that the sterile rivet and instrument be selectively detachably interengageable with facility when needed, and that the two may be selectively and intentionally disengaged when thought to be necessary by the surgeon, but not easily disengaged inadvertently or accidentally prior to the surgeon's conscious decision to disengage the insertion instrument from the rivet. This condition is important because during arthroscopic surgery, and even open surgery, visibility into the incision is limited and it is important that the surgeon have the assurance that the rivet will not inadvertently be disengaged prematurely.

Figure 37:
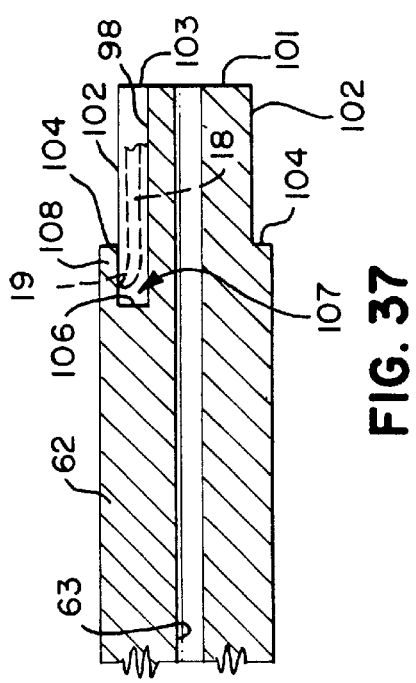
FIG. 37 is a fragmentary cross-sectional view of the rivet-rotating driver embodiment illustrated in FIG. 36, taken in the plane indicated by the line 37—37 in FIG. 36, and illustrating the manner in which a rivet lug is frictionally retained under the lip formed to receive it.
Figure 36:
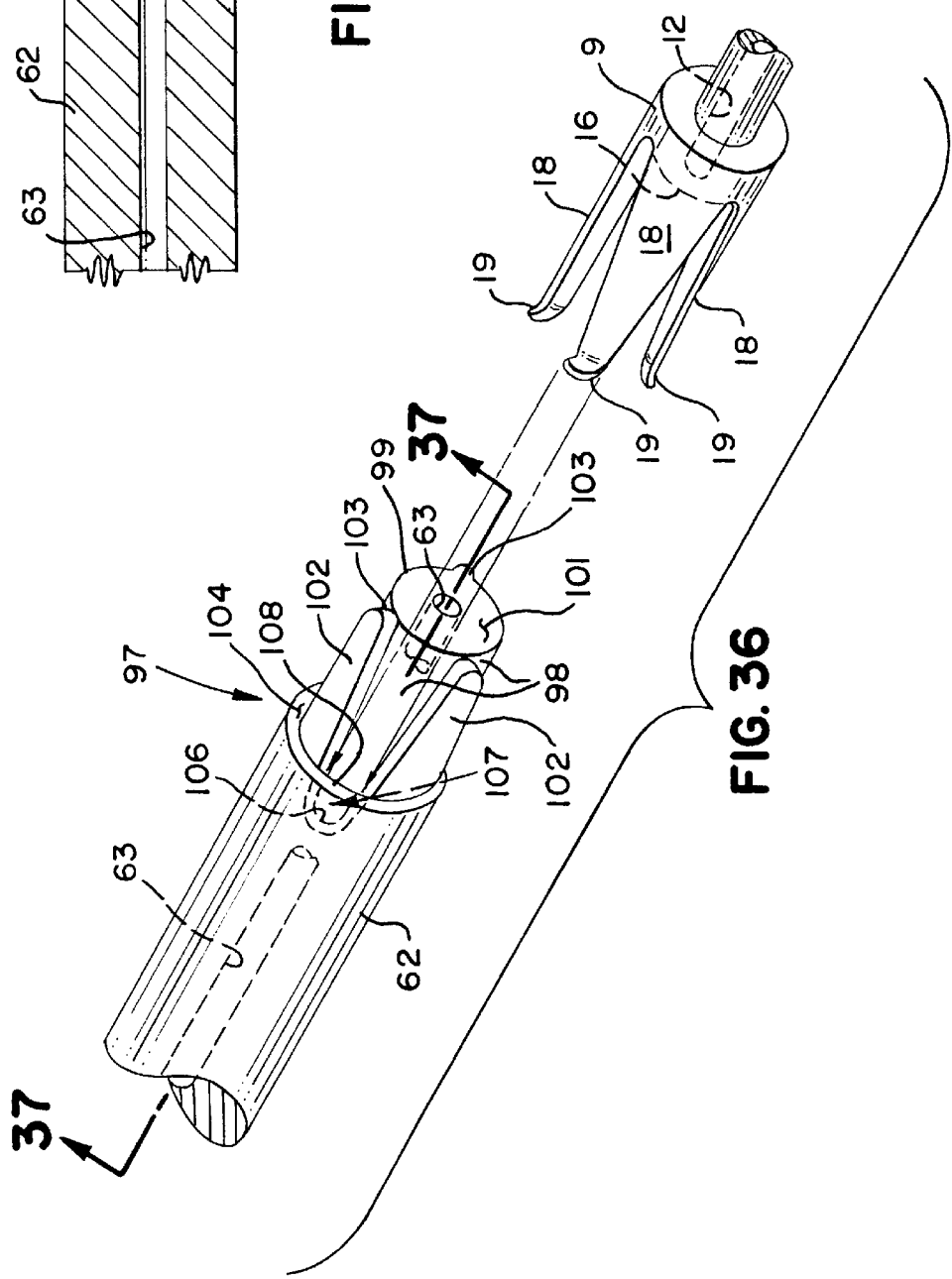
FIG. 36 is a fragmentary perspective view of a second embodiment of a rivet-rotating driver formed on the distal end of the rivet insertion instrument.

A second condition is that the selectively detachable union between the insertion instrument and the rivet enable imposition of a rotational moment on the threaded rivet so that, merely by its rotation and without the imposition of an axially directed force, the rivet be drawn progressively into the bone mass into which it is to be implanted. Thirdly, it ought not be required that the surgeon impose an undue axially directed force on the insertion instrument and rivet to maintain the union and impose the rotational moment on the rivet. This is important because the less axially directed force is exerted, the more tactile sense the surgeon will experience to know when the rivet has reached its fully implanted position. The insertion instrument described above and illustrated in FIGS. 26–35 adequately fulfills these three conditions. However, it should be understood that other socket configurations and cooperative structures may be designed that fulfill these conditions. Reference is now made to FIGS. 36 and 37, wherein there is illustrated a second embodiment of the insertion instrument 61 formed with a rivet driving head designated generally by the numeral 97 that retains the rivet selectively detachably mounted on the insertion instrument against relative rotation therewith, while enabling the imposition of a rotational moment on the rivet by digital rotation of the insertion instrument. Like the socket structure 64 and drive element 80 illustrated in FIGS. 26–35, the drive head 97 engages the rivet in a manner that enables rotation of the rivet without the imposition of an undue axially directed force or pressure on the insertion instrument or rivet.

Referring to FIGS. 36 and 37, it will be seen that the drive head 97 is formed integrally on the distal end of the tubular body 62, preferably by electric discharge machining, but which may be formed by other more conventional milling operations. The drive head is configured to fit snugly over the proximal ends of the lugs 18 of the rivet, with each of the lugs fitting snugly into a complementarily configured generally triangular recess 98 formed in the outer periphery of a centrally disposed cylindrical shaft 99 having an annular end face 101 through which the bore 63 extends.

There are three recesses 98, spaced circumferentially 120 degrees about the periphery of the shaft 99, each of the triangular configured recesses being defined on the one hand by the cylindrical outer periphery of the shaft 99, and on opposite sides by spaced triangular configured rib members 102, also spaced symmetrically on 120 degree circumferential intervals, and extending axially from their apex ends 103 coincident with face 101 of the shaft 99 to the annular end face 104 with which the ribs merge integrally to form a unitary drive head. At its proximal apex end remote from the distal face 101 of the shaft 99, each of the recesses extends beyond the annular face 104 to terminate at the bottom wall 106 of a pocket 107, each configured to receive the associated flared end of one of the lugs 18.

As previously explained, to mount the rivet on the insertion instrument, the flared ends of the lugs are elastically constricted radially inwardly sufficiently that the flared ends of the lugs may be projected into the pockets formed between the lip portions 108 and the radially inwardly spaced peripheral surface of the shaft 99 at the occurrence of each of the pockets. When the constricting force on the lugs is released, the elastically resilient lugs spring radially outwardly, resiliently impinging on the associated lip portions 108 to frictionally retain the rivet on the distal end of the insertion instrument. It should be understood that the distance between the annular face 101 of shaft 99 and the bottom 106 of the lug-receiving pocket 107 is such as to accommodate the full length of each of the lugs, with the annular end face 101 abutting the upper surface 16 of the rivet head 9. Since the edges of the lugs abut the associated ribs 102, it will be seen that rotation of the insertion instrument imposes a rotational force on the long edges of each of the lugs, thus effecting rotation of the rivet to drive it into the bone without the imposition of an axially directed force or pressure imposed on the insertion instrument.

It should also be understood that because the rivet is provided with an elongated bore 12 that corresponds axially with the bore 63 in the insertion instrument body 62, the rivet, detachably mounted on the end of the insertion instrument, may now be inserted, together with the insertion instrument, over the K-wire and into the guide sheath provided by the soft tissue positioning instrument, and advanced along the K-wire until the lower end 13 of the rivet passes through the soft tissue mass and impinges against the cancellous bone underlying the soft tissue mass. In passing through the soft tissue mass, it may be necessary to rotate the rivet several times to effectively take advantage of the screw threads on the rivet to draw the rivet through the mass of soft tissue with minimum trauma to the tissue. In this regard, it is important to note that the mass of soft tissue is still being held stationary by the lugs 37 and 38 of the tissue positioning instrument, and by the K-wire which passes through the mass of soft tissue and is still embedded in the cancellous bone tissue. The mass of soft tissue is therefore held securely in proper position as the threaded rivet shank passes through the soft tissue mass to impinge on the bone.

Because the rivet is still mounted on the end portion of the insertion instrument, and restrained against inadvertent axial displacement by friction, and restrained against rotation relative to the insertion instrument by projection of the ribs 102 between the lugs 18, it will be clear that when the end 13 of the rivet impinges on the bone surface, continued rotation of the insertion instrument will effect threaded engagement of the rivet shank with the cancellous bone and will progressively draw the rivet shank into the bone until the undersurface 17 of the rivet head impinges on the bone surface.

When this degree of implantation of the rivet is achieved, the surgeon will feel the increased resistance to rotation, and will know that the rivet has been seated at its maximum depth. At this point, the surgeon wants to know the spacial orientation of the lugs 18 in relation to the mass of soft tissue and other structures of the body. If the head 93 of the insertion instrument is triangular as in FIG. 28, the surgeon will immediately know the disposition of the lugs 18 because they correspond to the position of the apexes. If the surgeon is not satisfied with the spatial disposition of the lugs, the surgeon may of course rotate the rivet counter-clockwise to rearrange the spacial disposition of the lugs 18. On the other hand, if the head 93 of the insertion instrument is cylindrical as discussed above, all that is required is that the surgeon note the positions of the embossed or raised index marks on the head which correspond to the spacial disposition of the lugs 18, and be guided by that disposition in rearranging or not rearranging the position of the lugs 18. When the surgeon is satisfied that the lugs are in proper position, a slight intentional tug on the insertion instrument overcomes the frictional forces retaining the rivet against axial displacement, and the insertion instrument may be withdrawn from the outer sheath formed by the tissue positioning instrument.

Figure 5:
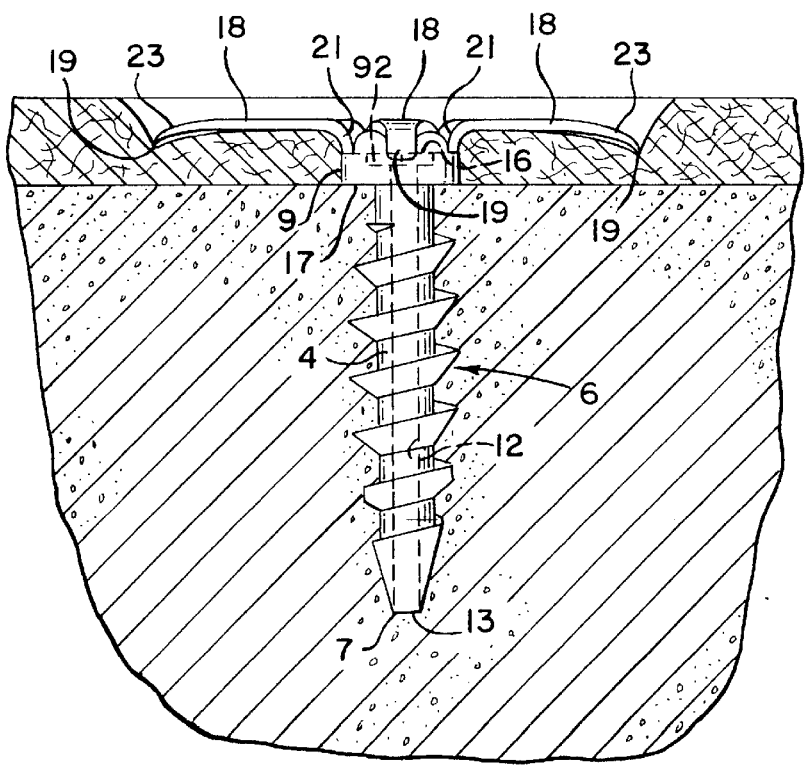
FIG. 5 is a side elevational view of the rivet in its second or ultimate configuration in which the head of the rivet has been reformed to clamp the soft tissue to the bone at the soft tissue attachment site.
Figure 8:
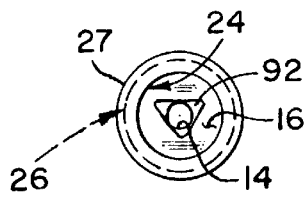
FIG. 8 is a top plan view of the partially fabricated rivet of FIG. 7.

Following withdrawal of the rivet insertion instrument, it will of course be apparent that while the rivet is set in the bone, it must still be permanently reformed by spreading of the lugs 18 into soft tissue clamping position as illustrated in FIGS. 3 and 5. To accomplish that end, reference is made to FIGS. 38–44 wherein there is shown three different lug forming instruments, two of which are designated generally by the numeral 112 (FIGS. 38 and 40) and differing only slightly from one another, and the third being designated generally by the numeral 113 and illustrated in FIGS. 42–44. Accordingly, except for the different structure in each, the same reference numbers are applied to identical structure in each instrument. Referring first to the lug forming instrument illustrated in FIGS. 38 and 39, it is seen that this lug-forming instrument includes an elongated tubular ram body 114 having a driving head 116 on one end and provided with a centrally disposed elongated bore 117 sized to slidably accommodate the K-wire that still remains embedded in the soft tissue and the underlying bone. It will of course be understood that the soft tissue positioning instrument 31 (FIGS. 12–18) has been withdrawn upon setting of the rivet. Formed on the distal end of the tubular ram body 114 is a cylindrical axially extending limit head 118 that is smaller in diameter than the tubular ram body 114 to form an annular ram shoulder 119.

The limit head 118 is sized so that its cylindrical outer diameter is smaller than the distance between the associated lugs 18. Its length is gauged to be shorter by about 0.039 of an inch than the length of the lugs 18. That relationship results in the proximate ends of the lugs 18 when in their preformed relationship as illustrated in FIG. 1 being abutted by the annular ram shoulder 119 when the forming instrument is advanced along the K-wire and placed against the rivet head. This relationship is illustrated in greatly enlarged form in FIG. 45.

Figure 4:
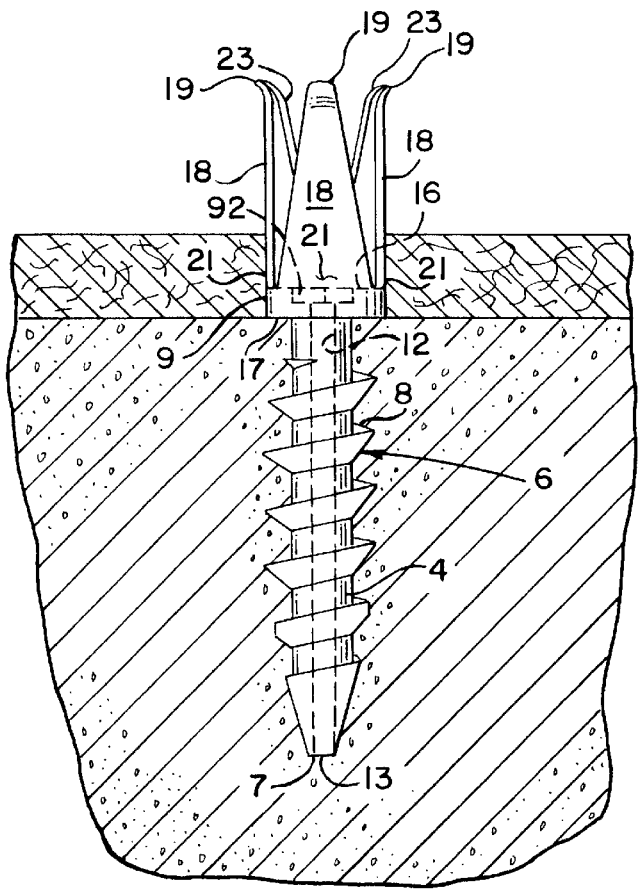
FIG. 4 is a side elevational view of the rivet in its first or initial configuration shown fully embedded in bone and projecting through soft tissue prior to being reformed into its second or ultimate reformed soft tissue clamping configuration.

Thus, after the rivet is set in the bone as shown in FIG. 4, and the insertion instrument and tissue positioning instruments are withdrawn, the tubular ram body 114 is fitted over the K-wire and advanced therealong until the ram shoulder 119 comes into physical contact with the ends 19 of the lugs 18. That physical contact has been made will be apparent to the surgeon from his tactile sense, by his sense of hearing and by the fact that the forming instrument cannot be digitally inserted further because it has encountered the abutment formed by the ends of the lugs 18. At this juncture the limit head remains spaced from the rivet head upper surface 16 by about 0.039 of an inch.

At this point, the surgeon utilizes a mallet (not shown) to strike one or more appropriate blows to the head 116 of the forming instrument. The result of such blows is illustrated in FIG. 47 where it is seen that driving the tubular ram body against the ends of the lugs 18 causes the lugs to simultaneously permanently bend at their bases and spread radially outwardly. As the ram body continues to move toward the head 9 of the rivet, the lugs are driven outwardly until the end surface 121 of the limit head engages the upper surface 16 of the head 9, thus preventing further advance of the initial or #1 ram body equipped with the longer limit head as illustrated in FIG. 33.

It will thus be seen that while use of the initial #1 ram body illustrated in FIG. 38 has caused the three lugs to be permanently flared outwardly, they have not been flared to the degree desired to effect a clamping function on the mass of soft tissue. The flaring of the lugs has however conditioned the lugs for further flaring utilizing the second or #2 forming instrument illustrated in FIG. 40. As shown, the #2 or second forming instrument is identical to the #1 or initial forming instrument with the exception that the limit head 122 on this instrument is of the order of 0.053 of an inch in length. Thus, following removal of the #1 forming instrument, the forming instrument #2 is slid onto the K-wire and inserted into the incision and against the partially flared lugs 18 and, through one or more blows of the mallet, the surgeon drives the forming instrument against the inner peripheries of the partially flared lugs 18 until the instrument progresses to the point that the limit head 122 comes into contact with the upper surface 16 of the rivet head 9. This degree of displacement of the forming instrument places the lugs 18 in substantially a permanently horizontal or perpendicular attitude in relation to the longitudinal axis of the rivet, and in soft tissue clamping position.

Nevertheless, to ensure that the lugs 18 are truly perpendicular to the longitudinal axis of the rivet, or perhaps, if the need presents itself because of the nature, position and thickness of the mass of soft tissue, depressed beyond the position of perpendicularity, the #3 or third forming instrument 113 illustrated in FIGS. 42–44 may be utilized by the surgeon. As illustrated in the drawing, the cylindrical ram rod 123 of this forming instrument 113 is formed without a central bore and without a limit head. Instead the end surface 124 of the ram rod 123 is provided with a transverse slot 126 having a width sufficient to accommodate the width of each of the lugs 18. When it is thought necessary to use this instrument, the surgeon, having first removed the K-wire to facilitate manipulation of the slotted end of the instrument, inserts the slotted end of the ram rod 123 into the incision and through tactile sense aligns the transverse slot 126 in turn with each of the lugs 18 and strikes one or more blows to individually depress each lug 18 permanently to the desired degree.

In this procedure, it will of course be apparent that the surgeon manipulates the slotted end of the forming instrument in a manner that may be out of alignment with the longitudinal axis of the rivet so that each lug may be individually depressed without interference from the head 9 of the rivet. It should of course be understood that in some instances it may be preferable that the lugs 18 be at different heights, i.e., not in a common plane, and this decision is one the surgeon must make after careful consideration of all of the factors involved to achieve a successful re-attachment of the soft tissue to the bone. Following proper placement of the three lugs, the surgeon withdraws the #3 forming instrument 113 and appropriately closes and dresses the incision.

While it is not expected that the rivet will ever have to be removed, it is of course possible that unforseen circumstances may require removal of the rivet. Such removal may be effected immediately following its implantation while the incision is still open, or it may be effected at a later date, as the need arises. If removal of the rivet is dictated immediately following insertion and prior to reformation of the soft tissue retension lugs 18, all that need be done is to re-insert the K-wire, and re-insert the rivet insertion instrument 61 with the triangular drive 80 to re-engage the rivet. Upon re-engagement, counterclockwise rotation of the rivet will effectivey withdraw the rivet from the bone.

On the other hand, if removal of the rivet must be effected after the bendable soft tissue retension lugs 18 have been spread into their soft tissue clamping position as illustrated in FIGS. 3 and 5, the K-wire is again inserted through the still open incision so that it penetrates the central passageway of the rivet. Next, a suitably configured grapnel instrument (not shown) in a form having three curved tines adapted to be inserted underneath the correspondingly positioned lugs 18 is inserted over the K-wire and the tines are engaged under the lugs 18 in such a manner that rotation of the instrument effects reformation of the lugs 18 into their initial parallel attitude as illustrated in FIG. 1, or nearly into such parallel attitude.

This procedure will of necessity impose a rotary moment on the lugs and on the rivet to which they are integrally attached. Accordingly, since it is not desired that the lugs be rotated while in their extended attitude as illustrated in FIGS. 3 and 5 because of the trauma that will occur to the soft tissue over which they are clamped, if this procedure becomes necessary, it is preferred that the grapnel instrument be rotated clockwise so that the threaded shank of the rivet and the head 9 thereof bearing on the bone surface will prevent rotation of the rivet and the lugs extending radially therefrom. Sufficient force is then exerted on the lugs to again reform them into parallel position. The grapnel instrument is then withdrawn, and the insertion driver instrument 61 is re-inserted to engage the rivet head and the recess 92. Thereafter, counterclockwise rotation of the rivet by the instrument will effectively withdraw the rivet from the bone without traumatizing the soft tissue through which it passes.

Ideally, the grapnel instrument is designed so that following clockwise rotation of the tines to reform the lugs into their initial parallel position, the grapnel instrument may then be rotated in a counterclockwise direction so as to impose a rotary moment on the rivet to withdraw it directly from the bone without the necessity of withdrawing the gragnel and re-inserting the rivet insertion instrument 61 to withdraw the rivet.

Alternatively, the lugs may be individually grasped, as with forceps, severed at their roots where they join the head 9, and each of the severed lugs lifted out of the incision with the forceps. The insertion instrument 61 may now be re-inserted to engage the rivet, which may then be rotated counterclockwise by rotation of the insertion instrument. The extracted rivet is of course discarded and the surgeon proceeds to insert another rivet either in the same location or a different location.

Having thus described the invention, what is believed to be new and novel and sought to be protected by letters patent of the United States is as follows.

I claim:

1. A metallic rivet for attaching soft tissue to bone tissue, comprising:
   a) an elongated cylindrical tubular unitary body symmetrical about a longitudinal axis and including an exteriorly threaded shank portion having a conically tapered distal end portion and a cylindrical integral head at its proximal end and a clamp portion integral with said head and including a plurality of circumferentially spaced longitudinally extending arcuate lugs the free end of each of which is flared radially outwardly, and
   b) a triangular drive recess formed in said head and oriented so that each apex thereof corresponds circumferentially with an associated arcuate lug;
   c) each said lug being configured generally as an isosceles triangular member having its base integral to said head and its apex end flared radially outwardly to form a surface inclined to the longitudinal axis of the cylindrically tubular unitary body, said apexes of the generally triangular lugs being arranged in a circular array spaced axially from said head, the arcuate spacing between said apexes substantially corresponding to the arcuate length of the base integral with the head.

2. A rivet for attaching soft tissue to bone tissue, comprising:
   a) an elongated unitary body symmetrical about a longitudinal axis and including a shank portion adapted to be anchored in said bone tissue and a clamp portion adapted to impale said soft tissue;
   b) means on said shank portion for retaining said rivet anchored in said bone tissue;
   c) means on said clamp portion selectively permanently reformable in situ to extend radially in relation to said longitudinal axis to overlie said soft tissue whereby to clamp said impaled soft tissue to said bone tissue;
   d) said means on said clamp portion selectively reformable in situ to extend radially in relation to said longitudinal axis comprises a plurality of circumferentially spaced initially longitudinally extending lugs;
   e) said lugs and the spaces therebetween being generally triangular, and the proximal ends of the lugs remote from said shank portion are flared radially outwardly to form surfaces inclined to the longitudinal axis of the unitary body.

3. The rivet according to claim 2, wherein said shank portion is provided with a head at one end and said clamp portion extends axially from said head in a direction opposed to said shank portion.

4. The rivet according to claim 3, wherein said shank portion including said head are provided with an elongated cylindrical passageway coaxially disposed about said longitudinal axis, and a drive recess asymmetric to said elongated cylindrical passageway is formed in said head symmetrically about said longitudinal axis.

5. The rivet according to claim 2, wherein said means on said shank portion for retaining said rivet anchored in said bone tissue comprises a spiral screw thread.

6. The rivet according to claim 2, wherein said elongated unitary body is provided with an elongated passageway coaxially disposed about said longitudinal axis.

7. The rivet according to claim 2, wherein said shank portion is conically tapered at one end.

8. The rivet according to claim 7, wherein said shank portion is conically tapered at its end remote from said clamp portion extending axially from said head.

9. The rivet according to claim 2, wherein said shank portion is provided with a head at one end, and said plurality of circumferentially spaced longitudinally extending lugs are integral with said head and extend axially therefrom.

10. The rivet according to claim 2, wherein said initially longitudinally extending lugs prior to reformation are arranged in a circular array symmetrical about said axis and parallel to each other and to said longitudinal axis and when reformed to extend radially are substantially perpendicular to the longitudinal axis.

11. A rivet for attaching soft tissue to bone tissue, comprising:
   a) an elongated unitary body symmetrical about a longitudinal axis and including a shank portion adapted to be anchored in said bone tissue and a clamp portion adapted to impale said soft tissue;
   b) means on said shank portion for retaining said rivet anchored in said bone tissue;
   c) means on said clamp portion selectively permanently reformable in situ to extend radially in relation to said longitudinal axis to overlie said soft tissue whereby to clamp said impaled soft tissue to said bone tissue;
   d) said means on said clamp portion selectively reformable in situ to extend radially in relation to said longitudinal axis comprises a plurality of circumferentially spaced initially longitudinally extending lugs;
   e) said shank portion being provided with an integral head having an outer cylindrical periphery, and said lugs are integral with said head and extend axially therefrom in a circular array; and
   f) each said lug being configured generally as an isosceles triangular member having its base integral to said head and its apex end flared radially outwardly to form a surface inclined to the longitudinal axis of the unitary body, said apexes of the generally triangular lugs being arranged in a circular array spaced axially from said head, the arcuate spacing between said apexes substantially corresponding to the arcuate length of the base integral with the head.

12. A rivet for attaching soft tissue to bone tissue, comprising:
   a) an elongated unitary body symmetrical about a longitudinal axis and including a shank portion adapted to be anchored in said bone tissue and a clamp portion adapted to impale said soft tissue;
   b) means on said shank portion for retaining said rivet anchored in said bone tissue;
   c) means on said clamp portion selectively permanently reformable in situ to extend radially in relation to said longitudinal axis to overlie said soft tissue whereby to clamp said impaled soft tissue to said bone tissue;
   d) said means on said clamp portion selectively reformable in situ to extend radially in relation to said longitudinal axis comprises a plurality of circumferentially spaced initially longitudinally extending lugs;
   e) said shank portion being provided with an integral head having an outer cylindrical periphery, and said lugs are integral with said head and extend axially therefrom in a circular array; and
   f) each said lug being configured generally as an isosceles triangle having its apex integral to said head and its base flared radially outwardly to form a surface inclined to the longitudinal axis of the unitary body, said bases of the triangular lugs being arranged in a circular array spaced axially from said head, the arcuate spacing between said bases substantially corresponding to the arcuate length of the apex integral with the head.

13. A metallic rivet for attaching soft tissue to bone tissue, comprising:
   a) an elongated cylindrical tubular unitary body symmetrical about a longitudinal axis and including an exteriorly threaded shank portion having a conically tapered distal end portion and a cylindrical integral head at its proximal end and a clamp portion integral with said head and including a plurality of circumferentially spaced longitudinallly extending arcuate lugs the free end of each of which is flared radially outwardly, and
   b) a triangular drive recess formed in said head and oriented so that each apex thereof corresponds circumferentially with an associated arcuate lug;
   c) each said lug being configured generally as an isosceles triangular member having its apex integral with said head and its base flared radially outwardly to form a surface inclined to the longitudinal axis of the unitary body, said bases of the triangular lugs being arranged in a circular array spaced axially from said head, the arcuate spacing between said bases substantially corresponding to the arcuate length of the apex integral with the head.

14. The rivet according to claims 3, 5, 6, 7, 4, 9, 2, 11, or 12, wherein said rivet is fabricated from metal.

15. The rivet according to claims 3, 5, 6, 7, 4, 9, 2, 11, or 12, wherein said rivet is fabricated from medical grade stainless steel.

16. The method of attaching soft tissue to bone tissue through use of surgical procedures, comprising the steps of:
   a) exposing to view the area of the bone tissue to which the soft tissue is to be attached;
   b) securing anchor means having a reformable head portion to the exposed bone tissue in the area of the bone tissue to which the soft tissue is to be attached;
   c) impaling on said reformable head portion of the anchor means the soft tissue to be attached to the bone tissue;
   d) reforming in situ the head portion of the anchor means to clamp and retain the soft tissue in intimate contact with the area of the bone tissue surrounding the anchor means whereby said soft tissue may attach itself to the associated bone tissue through natural regenerative healing processes;
   e) said head portion of the anchor means over which said soft tissue is impaled initially comprising a plurality of circumferentially spaced parallel lugs integral with said anchor means and symmetrical about a central longitudinal axis, and subsequent to impalement of said soft tissue over said head portion, said lugs are reformed to lie perpendicular to said central longitudinal axis distally from the surface of the bone tissue and in clamping association with the soft tissue.

17. The method according to claim 16, wherein said bone tissue is exposed to view through arthroscopic surgery.

18. The method according to claim 16, wherein said anchor means is embedded below the surface of said bone tissue to which the soft tissue is to be re-attached, and said reformable head portion projects from the surface of said bone tissue.

19. The method according to claim 16, wherein said anchor means is formed from metal.

20. The method according to claim 16, wherein a bore is formed in the bone tissue in the surface area thereof to which the soft tissue is to be attached, and said anchor means is embedded in said bore in a manner to leave said head portion protruding from the surface area of said bone tissue in which said bore is formed.

21. The method of attaching soft tissue to bone tissue through use of surgical procedures, comprising the steps of:
   a) exposing to view the area of the bone tissue to which the soft tissue is to be attached;
   b) securing anchor means having a reformable head portion to the exposed bone tissue in the area of the bone tissue to which the soft tissue is to be attached;
   c) impaling on said reformable head portion of the anchor means the soft tissue to be attached to the bone tissue;
   d) reforming in situ the head portion of the anchor means to clamp and retain the soft tissue in intimate contact with the area of the bone tissue surrounding the anchor means whereby said soft tissue may attach itself to the associated bone tissue through natural regenerative healing processes;
   e) said anchor means including an elongated tubular structure having inner and outer peripheral surfaces, said inner peripheral surface constituting a guide portion and said outer peripheral surface constituting a bone tissue engaging surface, and said head portion of the anchor means over which said soft tissue is impaled initially comprises a plurality of circumferentially spaced parallel lugs integral with said anchor means and symmetrical about a central longitudinal axis and subsequent to impalement of said soft tissue over said head portion said lugs are reformed to lie substantially perpendicular to said central longitudinal axis distally from the surface of the bone tissue and in clamping association with the soft tissue.

22. The method according to claim 21, wherein a bore is formed in said bone tissue in the area thereof to which said soft tissue is to be attached, a guide rod is inserted into said bore, said anchor means is slidably arranged on said guide rod and superimposed over said bore, a drive instrument is slidably and rotatably arranged on said guide rod and engaged with said anchor means and manipulated to drive said anchor means into engagement with said bore whereupon said drive instrument is removed from said guide rod, a forming instrument is slidably and rotatably engaged with said guide rod and manipulated to impose a laterally outwardly directed force on each of the lugs of said head portion, whereby said lugs are reformed to lie in a common plane perpendicular to the central longitudinal axis of said anchor means, whereupon said forming instrument is removed and the incision formed to expose said bone tissue is closed.

23. The method of attaching soft tissue to bone tissue through use of surgical procedures, comprising the steps of:
   a) exposing to view the area of the bone tissue to which the soft tissue is to be attached;
   b) securing anchor means having a reformable head portion to the exposed bone tissue in the area of the bone tissue to which the soft tissue is to be attached;
   c) impaling on said reformable head portion of the anchor means the soft tissue to be attached to the bone tissue;
   d) reforming in situ the head portion of the anchor means to clamp and retain the soft tissue in intimate contact with the area of the bone tissue surrounding the anchor means whereby said soft tissue may attach itself to the associated bone tissue through natural regenerative healing processes;
   e) The surface area of the exposed bone from which soft tissue avulsion has occurred being decorticated to expose raw cancellous bone, thereafter mobilizing the soft tissue to contiguously overlie the exposed raw cancellous bone, driving a K-wire through the soft tissue that has been mobilized and into the underlying raw cancellous bone to retain the soft tissue in position, inserting a soft tissue positioning instrument over the K-wire and into penetrating engagement with the soft tissue and manipulating the soft tissue positioning instrument to adjust the position of the soft tissue to place it where it is to be permanently reattached, thereafter attaching a sterile anchor means in the form of a cannulated rivet to a rivet insertion instruments threading the rivet and rivet insertion instrument over the K-wire and telescopically into the soft tissue positioning instrument to impale the soft tissue with the rivet and place the distal end thereof into contact with the raw cancellous bone, rotating the rivet through rotation of the rivet insertion instrument until the rivet is maximally embedded in the bone, withdrawing the rivet insertion instrument from the K-wire and the soft tissue positioning instrument, withdrawing the soft tissue positioning instrument while retaining the K-wire embedded in the bone, inserting a first forming instrument over the K-wire into contact with parallel lugs forming the reformable head of the rivet, thereafter delivering impacts as necessary to the first forming instrument to partially radially displace the lugs, thereafter withdrawing the first forming instrument and inserting a second forming instrument into contact with the partially reformed lugs and delivering impacts as necessary to further radially displace the lugs into a common plane wherein the radially displaced lugs clamp the soft tissue to the raw cancellous bone area, thereafter withdrawing the second reforming instrument, and thereafter withdrawing the K-wire and closing the incision.

* * * * *